United States Patent [19]

Sklar et al.

[11] Patent Number: 5,098,426
[45] Date of Patent: Mar. 24, 1992

[54] METHOD AND APPARATUS FOR PRECISION LASER SURGERY

[75] Inventors: H. Alfred Sklar, San Francisco; Alan M. Frank, Livermore, both of Calif.; Olga M. Ferrer, Miami, Fla.; Charles F. McMillan, Livermore, Calif.; Stewart A. Brown, Livermore, Calif.; Fred Rienecker, Pleasanton, Calif.; Paul Harriss, Livermore, Calif.; Steven Schiffer, San Francisco, Calif.

[73] Assignee: Phoenix Laser Systems, Inc., San Francisco, Calif.

[21] Appl. No.: 307,315

[22] Filed: Feb. 6, 1989

[51] Int. Cl.$^5$ .............................................. A61N 5/02
[52] U.S. Cl. .......................................... 606/5; 606/4; 606/10; 606/13; 128/630; 128/395; 364/413.02; 364/413.13; 351/209; 219/121.60; 219/121.62; 219/121.85
[58] Field of Search ............... 128/630, 633, 653, 664, 128/665, 395; 606/2, 4, 5, 6, 10, 12, 13; 364/413.01, 413.02, 413.13; 351/200, 205, 209, 209–215; 219/121.60, 121.62, 121.67, 121.69, 121.73, 121.74, 121.75, 121.78, 121.79, 121.81, 121.83, 121.85

[56] References Cited

U.S. PATENT DOCUMENTS

| 4,538,608 | 9/1985 | L'Esperance | 128/345 |
|---|---|---|---|
| 4,579,430 | 4/1986 | Bille | 351/206 |
| 4,669,466 | 6/1987 | L'Esperance | 606/5 |
| 4,743,771 | 5/1988 | Sacks et al. | 250/560 |
| 4,848,340 | 7/1989 | Bille et al. | 606/4 |

FOREIGN PATENT DOCUMENTS 8707165 12/1987 World Int. Prop. O. .............. 606/4

Primary Examiner—David Shay
Attorney, Agent, or Firm—Thomas M. Freiburger

[57] ABSTRACT

A system for effecting precision laser surgery includes an intensified surgical video microscope directed at the tissue to be operated upon and having zoom capability. The surgical microscope presents a microscopic image on a video screen in front of the surgeon. Preferably, the video screen is divided into multiple separate sections, with the microscopic video image in one section and precise cross sectional and plan views indicating location presented in the other sections of the screen. These additional views may be generated using Moire interferometry by projecting a Ronchi ruling on the surface of the tissue, in viewing the projection with a camera to obtain all necessary information for contour tracking of the subject surface. Interior elements and interfaces of, for example, the eye are also sensed by a light beam and precisely located and mapped by a computer forming a part of the device. The imaging system of the invention enables the surgeon to have before him abundant visual information on the video screen with indication of precisely where, in three dimensions, a focused surgical laser beam is directed at any time. The system also includes tracking system for following the movements of the subject tissue, for example an eye during surgery. The tracking system is fast enough to track such movement, preferably at the maximum repetition rate of the laser plus a sufficient margin for safety, but at all times faster than the frame rate for the video displays at which the video screen is retraced.

44 Claims, 12 Drawing Sheets

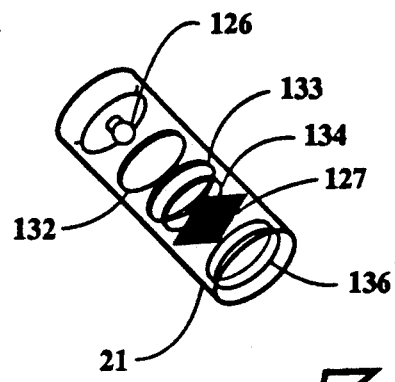
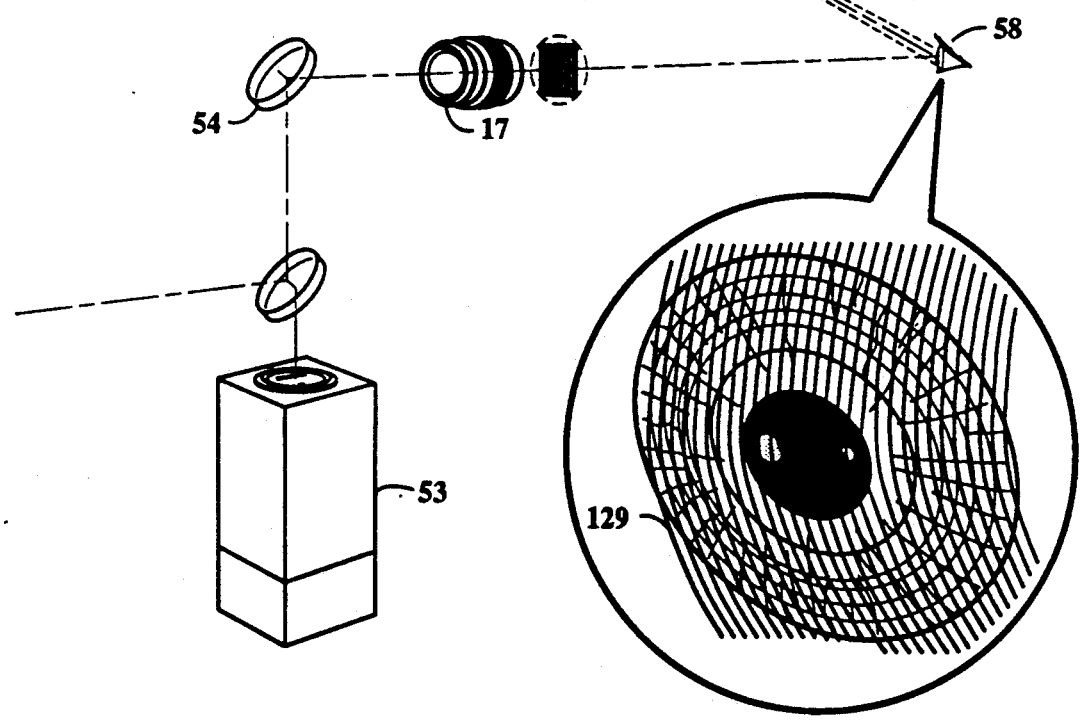
FIG. 7
FIG. 8

METHOD AND APPARATUS FOR PRECISION LASER SURGERY

BACKGROUND OF THE INVENTION

The invention relates to surgical methods and apparatus, and in particular the invention is directed to improved methods and apparatus for precision laser surgery. In one preferred embodiment, the system of the invention is used for effecting precise laser eye surgery. In other embodiments the invention is applicable to non-surgical diagnostic procedures or non-medical procedures involving precision laser operations, such as industrial processes.

Beginning in approximately 1960, largely due to the work of Dr. Littman at Carl Zeiss, the first surgical microscopes were introduced. Prior to that time, surgeons who required a more magnified image of the region in which they sought to operate used a special set of loupes that have magnifying lenses attached to the lower portion of the spectacles, especially in ophthalmology but also in otoringology and other specialties. In other disciplines such as urology and internal surgery, barrel type endoscopes were used.

Due in part to the pioneering work of Dr. Joaquin Barraquer, the surgical microscope came into wide use in ophthalmology; at first for corneal transplant surgery and later for cataract surgery among other procedures. The levels of magnification, zooming capabilities, and definition of the work region provided the surgeon the means to better direct his surgical invasions. The end result was increasingly more accurate surgical procedures with less trauma to the patients and a lowered level of complications arising from surgery.

The early successes with now conventional surgical microscopes based on direct optics for observing a target image, gave rise to the creation of several ophthalmic study groups, most notably the International Ophthalmic Microsurgical Study Group ("IOMSG"), to promote new concepts and techniques in microsurgery. Since their inception in 1966, the invited reports presented at the IOMSG meetings have been published by Karger, Basel as their *Developments in Ophthalmology* series.

The advent of microsurgery brought on by the use of surgical microscopes rekindled interest in the ophthalmic community for the pioneering of increasingly more accurate surgical procedures. In their continued quest for accuracy and control, ophthalmologists eventually turned to another of the discoveries which occurred around 1960, the laser.

During the 60s, 70s, and 80s, lasers were used extensively in ophthalmology and have now become a commonplace tool in most surgical specialties' instrumentalia. There are several distinct advantages to the laser as a scalpel replacement which have come into evidence.

Since a laser's energy is composed of light photons, by selecting the wavelength of the laser emission to correspond to the preferential absorption band of an imbedded tissue, a laser can be deemed to perform "non-invasive" surgery, in that the surgeon need not perforate the overlying tissue layers in order to generate an effect at a prescribed depth.

Biological tissues are, however, broad band absorbers of energy, albeit not uniformly so. In practice therefore, "non-invasive" laser surgery corresponds to the effort to minimize the laser energy deposition onto the living tissues on the way to and directly behind the targeted tissues along the optical path of the laser beam when compared to the energy deposition at the intended target.

During the early 1980s, Dr. Aron-Rosa (U.S. Pat. No. 4,309,998) introduced a mode locked Nd:YAG laser for use in Ophthalmology which claimed to evidence plasma decay induced generation of outwardly expanding shock waves. Dr. Frankhauser (U.S. Pat. No. 4,391,275) claimed a somewhat similar result using a Q-switched Nd:YAG laser. Ultrashort pulsed lasers have now established themselves as the modality of choice for many surgical procedures where propagating thermal effects are to be suppressed.

In 1986, this approach was taken one step further by development of an excimer pumped dye laser (not to be confused with an excimer laser which, due to the highly energetic photons characteristic of ultraviolet lasers, are characteristically penetrative photoablative lasers—See Trockel, U.S. Patent Pending, Schneider and Keates, U.S. Pat. No. 4,648,400, Srinivasian, U.S. Pat. No. 4,784,135, and L'Esperance, U.S. Pat. No. 4,665,913) which could predictably cause plasma effects with significantly less pulse energy than previously demonstrated. (See Ferrer and Sklar, Vol. XIV, Developments in Ophthalmology, Karger 1987, and Troutman et al. in the same Volume and in Trans. of Am. Ophth. Soc. 1986).

Laboratory experiments conducted by the applicants herein (unpublished) showed that imbedded cavities of diameters smaller than 0.5 micrometers are possible provided that tightly contained plasmas could be generated with a less than 0.5 millijoule pulse. The importance of the smallness of the induced lesions is related to the accuracy and error tolerances which can be achieved by the guidance and delivery systems of surgical instruments using such lasers. Lasers today are varied. It is well appreciated that the limitations on the achievable accuracy and control of laser surgical instruments today is no longer paced by the development of laser technology, but by the imaging and tracking technologies needed to effectively use the laser.

An understanding of current practices and the range of instruments in use for target acquisition, target recognition, and target tracking is helpful in order to appreciate the limitations of the current technologies. The principal instruments used today, for example in ophthalmology, for targeting diagnostics and inspection are (1) the surgical microscope, (2) the slit lamp microscope, (3) the keratometer, (4) the pachymeter, (5) the corneoscope, (6) the specular microscope, (7) the A&B ultrasonic scanners, and (8) the fundus camera. (There is a host of additional equipment used to determine intra ocular pressure, tonometers, tensiometers, perimeters for visual field testing, and the various devices used to approximate the eye's refraction.) Items 1, 2, and 8 provide the surgeon with an image of his target. Items 3, 4, 5, 6, and 7 provide the surgeon with measurements of specific dimensions of a patient's eye and condition.

These instruments have proven efficacious to within previously acceptable tolerances.

It is an object of the present invention to accommodate much more demanding tolerances in laser surgery, particularly eye surgery but also for other medical specialties, through a method, apparatus and system for high-precision laser surgery which provides the surgeon "live" images essentially in real time, containing the full supporting diagnostic information about depth and position at which a surgical laser will be fired. In a computer, the full information content of a given signal is interpreted so as to provide this supporting diagnostic information, and the resulting accuracy achievable is within a few human cells or better. It is further within the scope of this invention to provide non-surgical tools for measurement of the entire refraction of the eye rather than relying solely on the approximate curvature (keratometric "k" readings) of the anterior surface of the cornea. This calls for curvature readings of all of the reflective surfaces of the eye and allows for measurement of astigmatism and accommodation between the various optical components of the eye.

SUMMARY OF THE INVENTION

In accordance with the present invention, a method, apparatus and system for carefully controlled and precision laser microsurgery includes a user interface which gives the physician ample and precise three dimensional visual information as to the topography of the area to be operated upon and as to the aiming location and depth penetration of the surgical laser beam.

The system is also useful for non-medical operations, such as industrial operations, wherein a focused laser beam is used to perform operations on an object subject to movement, with a high degree of precision.

In the user interface, a video screen is provided in front of the surgeon, and the screen may even be divided into four quadrants: one quadrant showing an image of cell walls in real time taken from a video camera based, zooming surgical microscope which may be capable of enlargement from 25 times to 500 times, for example. The surgical microscope image might show a region having a dimension of as small as the order of 100 microns, for example. This real-time video image is of tissue at the precise location and depth at which the surgical laser is currently directed, or, in the alternative, of critical cells directly posterior to the target which should be monitored to help assure no damage to these sensitive tissues (e.g., corneal endothelial cells posterior to, but along the optical axis of, a laser pulse). The surgical microscope may be used to scan different regions at different depths under the control of the surgeon/user, even though the laser is not yet being fired.

Two of the other quadrants of the video screen may be dedicated to computer-generated images showing cross sections through the tissues to be operated upon. The cross sections may be taken through two separate and orthogonal planes, or other cross sectional planes may be selected by the surgeon. Each computer-generated image may have a crossbar or other indicator showing precisely where the surgical laser is currently directed.

A fourth quadrant of the video screen may be dedicated to a computer-generated plan view, greatly enlarged but not to the extent of the surgical microscope view. In this last quadrant, and/or on any of the other cross sectional representations, there may be superimposed a "template" selected by the physician, for automatically controlling the path of the firing of the laser, to precisely control the size and location of the laser generated lesions to be formed in the course of the microsurgery. Thus, the surgeon may draw on a bank of prior experience and knowledge relating to a particular form of microsurgery, such as ophthalmic surgery directed to a particular type of correction. By laying the template in effect on the computer-generated image of the region, he can then execute a pre-stored program to automatically execute the surgery in a precisely controlled preselected manner. It should be noted, however, that without the accompanying three-dimensional targeting capability and the image stabilization means, the utility of template generated surgery would be severely limited either to non-sensitive tissues (where high three dimensional precision is not usually a consideration) or to relatively stationary or immobilized targets (not usually available at high magnification in a biological system which is "alive").

The accuracy of the apparatus and system of the invention preferably is within 5 microns, as determined by a closed loop system which incorporates actual measurement of the target position within the loop. (For example, a microstepper motor based assembly may have a single step resolution of 0.1 micron verified against a motor encoder, but thermal gradients in the slides may yield greater variations. Moreover, position of the slide can be verified via an independent optical encoder, but the random vibrations of the target can invalidate the relative accuracy of the motor.) Thus, the surgeon has knowledge of the shape of tissues within the field of view and the precise location of where he is aiming the instrument within those structures, within an accuracy of 5 microns. Such precision was not attainable in a systematic, predictable manner with any of the prior instruments or practices used. The present invention seeks to obviate and improve upon the need for binocular vision used to obtain stereoptic images.

In a preferred embodiment of the invention, the instrument provides the surgeon/user with the option of selecting any given cross sections of the three dimensional structures to be operated upon, and the contour levels of the structures. The focal point of the imaging assembly (precisely the same as the focal point of the focused laser pulse, which is only activated when deliberately fired), is also automatically displayed on each of the display screens. There is no need for a separate aiming beam, because the laser beam trajectory not only shares the same optical path with the imaging system, but both light paths pass coaxially through the same final focussing lens. Misalignment of two different light paths is therefore eliminated, and also eliminated is the necessity to verify whether two different light paths have a common focal plane or common focal point.

Once the user of the instrument has sufficient cross sectional representations of the structure and contour levels of the tissues to be operated upon, he can then draw onto the computer screen the intended therapeutic procedure. A number of different systems can be used for conveying to the computer the desired procedure. One is to use commercially available touch screens with a special light pencil. Alternatively, a trackball or joy stick can be used. The surgeon can then either draw freehand his proposed operation, or use some preprogrammed geometrical designs. Another system, described briefly above, is to superimpose on the patterns being displayed on the screen from the imaging information, a computer generated template of the desired surgical path. As discussed previously, a library of such templates can be developed a priori and via accumulating experience, and the ability to modify these templates to fit particular requirements of a given situation is provided to the surgeon/user. This is a very important feature since the operations intended by surgeons are often complicated and delicate. By first prescribing these templates, the surgeon has the ability to reflect as to the particular three dimensional shape of the lesion to be generated for that particular patient, for the proposed therapy, prior to commencing the procedure.

With lasers of increasingly higher repetition rate becoming available, the sometimes intricate patterns desired for a given surgical procedure can be accomplished much faster than the capabilities of a surgeon manually to aim and fire recursively. In prior systems and procedures, the surgeon would aim at a target, verify his alignment, and if the target has not moved, then fire the laser. He would then move on to the next target, and repeat the process. A limiting factor to the duration of the operation under these prior procedures was the surgeon's reaction time while he focusses in on a target, and the patient's movement while the surgeon finds his target and reacts to the target recognition by firing the laser. In contrast, with the instrument and system of the present invention, the motion of the patient is stabilized by use of a target acquisition and tracking system which allows the surgeon to predetermine his firing pattern on an image which is automatically stabilized over time. The only limitations in time with the system of the present invention relate to the repetition rate of the laser itself, and the ability of the tracking system to successfully stabilize the image to within the requisite error tolerances for safety and efficacy. In the latter category, tracking response rates of several times faster (as determined by safety and stability considerations) than the maximum repetition rate of the laser (and faster than the maximum frame rate of the display means) have been achieved in an embodiment of the invention for following the motion of the target. Faster total loop delay times are possible with the described embodiment of the invention, limited by the ultimate speed of the tracking detector and the mass of the tracking servo mirror. It has been determined that such closed loop target recognition and tracking should occur at least at 20 repetitions per second in order to provide a significant improvement over human reaction times, and preferably at speeds greater than 500 Hz in order to enable the instrument and surgeon to fire the laser most efficiently at a selected location and complete a surgical procedure in a reasonable time span.

Using the instrument of the present invention, the surgeon can predetermine a proposed pattern of therapeutic treatment, can compare the pattern to the actual tissues targeted, can reflect on the potential outcome of the procedure, can compare his proposed surgery with what other surgeons have done in similar situations, can compare his proposed course of action with theoretical models of structure relaxations, and can still have the assurance that when he is finally satisfied with the proposed procedure, he can push a button to cause the desired surgery to be carried out at a high rate of independently targeted shots per second, but at a rate less than the response rate of the tracking system and with an added factor of safety. This speed minimizes the risk during surgery of catastrophic patient motion. In prior systems, on the other hand, the surgeon could not consistently cut out imbedded patterns from tissue, which requires precision and connectivity, because his targeting mechanism relied exclusively on his ability to aim and shoot at a rapidly, randomly moving target. The surgeon did not have available a rapid, real-time tracking system for assuring reliability of location in the three dimensional firing procedure.

Safety is a very important consideration with laser surgery. In prior surgical systems and procedures, some safety shut off procedures for laser firing have depended upon human reaction time, such as a surgeon's foot pedal for disabling the instrument when a situation arises which would make firing unsafe. In ophthalmology, some instruments have relied as a safety feature on a pressure sensor where the patient's forehead normally rests during surgery. If insufficient pressure were detected by the sensor, the instrument would be disabled from firing.

Such prior safety systems have inherently had slow reaction times, and have not been able to react quickly enough to all of the various problems which can arise during a firing sequence. This is particularly true in ophthalmic surgery and critically for specific retinal surgical procedures. (The necessity for sophisticated safety interlocks for laser surgical instruments may not have become as clear in several other medical specialties as in ophthalmology due in part to the lack of safety rendering the procedure so unfeasible as to not warrant experimentation.) In contrast, the target capture and tracking system of the present invention makes available a new and highly dependable safety system. If for any reason, either prior to or during a given surgical procedure, the tracking system loses its target, the instrument is stopped from firing. Thus, in ophthalmic surgery, this safety subsystem will accommodate the problem of an eye blinking or other obstructions during surgery, a potentially dangerous problem which often arises.

The blinking eye exemplifies the functioning of aspects of the safety features of the present instrument and system. As the blinking eyelid comes into view of the imaging system, the topographic information on which the tracking system has been stabilizing the motions of the moving eye is significantly altered. The system then interrupts the preprogrammed firing sequence while maintaining in memory the topography it was previously working on, the template information selected by the surgeon, and the position at which the firing sequence was last executed prior to interrupt for that given template for that determined topography.

Once the blinking eyelid or other obstruction leaves the field of view, the target acquisition system can go back to recognizing the topography it was previously operating in and automatically place the laser focal point at the next position in the prescribed firing sequence. The surgeon may then use a switch to recommence the firing, so as to have time to verify that the target has indeed been recaptured. However, after more experience and confidence with the instrument, the surgeon may elect to override the manual switch for restart of the firing sequence so that the system automatically returns to the template prescribed firing sequence, without prompting.

The tracking subsystem of the invention serves two important purposes—it tracks and follows in real time (virtually "real time", i.e. delayed only by the speed of the electronics and the tracking mirror) the movements of the patient's tissue, not only the voluntary movements which can be damped with specialized treatment, but also the involuntary movements which are more difficult to control on a living specimen) and continuously re-presents an image of the same section of tissue at a closed loop speed equivalent to real time. Thus the surgeon/user is provided a continuous, substantially immobilized view of that tissue regardless of patient movements; and it further provides a fail-safe means for immediately stopping the action of the surgical laser beam in the event the tracking is lost, i.e. the tissue is not recognized by the computer stored image on which the tracking algorithm is following the motion, and the vision is not re-aimed at the appropriate tissue within the selected operating interval.

As mentioned above, previous conventional instruments available to the ophthalmic surgeon have included the corneoscope, the keratometer, and the pachymeter, for providing to the surgeon/user limited measurement information regarding the cornea of the eye. The corneoscope provides contour levels on the outer surface of the cornea, or corneal epithelial surface, derived from projected concentric illumination rings. The keratometer gives cross sectional curvatures of the epithelial surface layer resulting in an estimation of the diopter power of the front surface lens of the eye—the corneal epithelium surface. Only one group of points is examined, giving very limited information. Pachymeters are used to determine a center-axis thickness measurement of the cornea.

All of these prior instruments have required considerable time to derive the desired information for precision ophthalmic surgery, and it can be that all of these as well as additional instruments are needed by the surgeon/user to obtain sufficient information for high precision surgery. Therefore, operation in real time (as determined by the actual motions of the tissues targeted for therapy and by the fastest human response times to these motions) has not been possible with these conventional instruments. Further, the use of these instruments required near-total immobilization of the eye for precise laser eye surgery, or in the alternative the surgeon/user had to be satisfied with available inaccuracies; the immobilization methods determined the limitations on accuracy and effective dependability. Moreover, the instruments represented several different apparatus which do not combine into one smoothly operating instrument and are consequently not conducive to use during surgery, but rather before and after surgery.

The system, apparatus, and method of the present invention for precision laser surgery, particularly ophthalmic surgery, takes an entirely different approach. Continuously updated images, preferably video images, are presented to the surgeon/user as the surgery progresses, and these images contain all information, in three dimensions, needed for the surgeon to reliably and accurately conduct a given ophthalmic surgery procedure. Movements of the eye are followed by a tracking system which operates at least as fast as both the speed with which the video screen retraces video images and, using dedicated microprocessors, at closed loop refresh speeds greater than several times the maximum repetition rate of the laser. Tracking by following the subject eye tissue, i.e. recognizing new locations of the same tissue and readjusting the imaging system and the surgical laser aim to the new location at total operational speeds faster than the laser firing rate assures that the laser, when firing through a prescribed pattern, will not deviate from the prescribed pattern an unacceptable distance. In preferred embodiments of the invention, this margin of error distance is held within 5 microns in all situations during ophthalmic surgery, although with future use and experimentation it may be found that either more stringent or alternatively more lax error tolerances are desirable to improve overall performance.

In accordance with the invention, real time imaging and tracking is achieved using a tracking mirror which may be under the directional control of a piezoelectric or electromagnetic transducer, or other rapid servo device. The transducer adjusts the position of the mirror along two rotational axes at speeds on the target in excess of 30 microns per millisecond, based on microprocessor-provided information relating to the new location of the same tissue.

Preferably, an illumination light, the surgical laser beam and an intensified video surgical microscope are along the same optical axis, on which is also located the turning mirror for tracking the tissue. The surgical microscope provides a greatly enlarged image of the tissue at which the laser is directed, with a field adjustable from about 0.1 to 100 mm.

Separate cameras also share a portion of the optical path used by the surgical microscope, the laser, and the illuminator. At least the tracking mirror and a final focussing or front element lens are in this common optical path. The profiling camera obtains data from the position of a projected Ronchi ruling on and inside the eye, sufficient to generate the full range of information in three dimensions needed by the surgeon, for presentation on the video screen. The profiling camera also, in concert with the microprocessor and programming, records the position of certain features and finds and relocates those same features after the eye has moved. This information is also used by the microprocessor and programming to determine Z axis offsets in target position and to generate a command to the Z axis positioning drive to follow such target motions as detected by the profilometer camera. These motions will be analyzed and corrected by the motions of the front element of the objective lens.

Both the analysis of the Z axis offset and the corrective lens motions are slower than the X,Y analysis and motion of the tracking servo mirrors. However, the same information, microprocessor, and programming serve as a backup signal to the faster tracking servo mirror signal to be used for periodic verification of accuracy and, more specifically, as an absolute position reference whenever the tracking detectors fail to recognize the target or its location either because of extraneous impediments or because of the unforseen speed of random motions. In this case this same information initiating from the profilometer camera would be used to drive tracking servo mirror to turn the mirror appropriately so that the axis of the tracking camera is again directed toward the same center of view that existed before the movement occurred. Further, with the three dimensional mapping system of the invention, the tracking camera can recognize movements relating to changes in depth of a certain tissue feature from the final focussing lens. In response, the microprocessor and programming issue a command to the final focussing lens to adjust the focal point of the system, i.e. of the tracking camera, the surgical microscope, and the surgical laser so that these are again correctly focused at the required tissue feature position.

The tracking cameras preferably are linear array detectors that scan only one line of position. They are dedicated detectors which are not only extremely rapid, but since they accumulate less data than the profilometer camera, can be read out in less than 100 microseconds.

In a preferred embodiment of the invention, separate fast tracking and slow tracking loops are employed, as explained below. The fast tracking loop can use the linear array detectors, while the slow loop may use the profilometer camera information at the maximum attainable video frame rate.

It should be pointed out that not only patient-originated movements are accommodated and compensated for with the present system. The surgery itself, as it progresses, induces changes in the topography of features of the tissue. The tracking system follows what it recognizes as a given field of features.

By incorporating intensified cameras, the present instrument and system is of high sensitivity, requiring only low levels of illumination, and produces video images of high contrast and high resolution. Illumination levels are kept well within established safety levels for the human eye. With the optics of the present system the patient's tissue is observed from an appreciable distance, sufficient for comfort to the patient even during eye surgery, and sufficient to permit the surgeon/user ready access to the patient to insure safety, to reassure the patient, for access in case of emergency, or for any other reason which the surgeon/user may feel justifiable.

Zoom optics are included so that the physician can select a range of magnification for the video image, which may be from about, say, $25\times$ to $500\times$. Different zooming ranges may be appropriate for different types of surgical procedures while maintaining an overall zooming capability of approximately 20 fold.

Instruments useful conventionally for ophthalmic surgery have often used specular reflection techniques for detection of the location and measurement of ocular features. Basically, only the tear surface layer overlying the corneal surface epithelium was usually detectable and measurable by specular reflection light techniques. The reflected light signal is not normally sufficient for the inner surface topographic information extraction of the endothelium of the cornea, let alone for characterization of the three dimensional shape of the anterior and posterior capsules of the crystalline lens of the human eye in real time. Reflected light from the corneal endothelium would be of so low a light intensity as to be below the noise levels of real-time detection devices needed to capture the signal information with sufficient speed and definition to permit real-time tracking and display of inner surface topographies. Instruments which rely on extensive computer analysis based on single frame capture of corneal images do not provide the required closed loop response times needed for the surgical procedures encompassed by the present invention.

Further, since much of the eye tissue is not only transparent but approximately spherical, specular reflections are not available when viewing with an optical system of limited aperture from a set direction, for the entire surfaces of interest, let alone of the intervening regions between the reflecting surfaces where the actual surgery is usually, or preferentially, performed.

The system of the present invention uses a combination of specular and scattered light techniques for detecting and identifying reflecting surfaces, surface displacements, features, and shapes of the patient's tissue. This is particularly useful in the eye where it can prove difficult to differentiate, using strictly specular techniques, between the amorphous tear layer anterior to the cornea and the structured epithelial surface layer of the cornea. Even the cell walls of the endothelial cells of the cornea will scatter light. Thus, the intensified surgical microscope can produce an image of these actual cells by forming an image composed by detecting scattered light. The surgical microscope, as well as the tracking camera, substantially excludes specularly reflecting light by cross polarization. Other methods for damping specular reflections preferentially to scattered images are possible, but not considered as optimal in this embodiment of the invention.

Using these light detection techniques, the instrument and system of the present invention repeatedly presents to the surgeon/user the precise focal point of the imaging system and of the surgical laser for reliable control of laser surgery, particularly ophthalmic surgery. Full information of all pertinent features of the eye is presented to the surgeon, including the precise shape and location of all features such as the corneal epithelium and endothelium surfaces. New information is detected in this embodiment of the invention at speeds not less than the maximum repetition rate of the laser plus a comfortable safety margin, say ten times faster, and at all times not less than the frame rate of the video screen, e.g. 30 times per second for currently standard video rates. Much faster repetition times are possible in accordance with the invention.

Accordingly, in one embodiment of the present invention, a system for use in ophthalmic laser surgery includes a laser source having a beam having power capable of effecting a desired type of surgery in the ocular tissues, with optical path means for delivering the laser beam, including beam directing means for controlling the aim and depth of focus of the laser beam. The system includes three dimensional mapping means for sensing locations, shapes and features on and in a patient's eye in three dimensions, and for generating data and signals in accordance therewith. A display means receives signals from the three dimensional mapping means and presents to a surgeon/user images representative of the locations, shapes and features of the eye in real time. A position analysis means receives signals from the three dimensional mapping means, and recognizes the occurrence of changes of position of features of the eye, and an associated target tracking means searches for a feature and finds its new position after such a change of position, and generates a signal indicative of the new position. A tracking positioning means receives the signal and executes a change in the aim of the three dimensional mapping means to the new position of a feature in real time, to thereby follow the feature and stabilize the images on the display means, and simultaneously to adjust the aim of the laser beam to be directed at the new position of the feature targeted.

It is therefore among the objects of the present invention to greatly improve the accuracy, speed, range, reliability, versatility, and efficacy of laser surgery, particularly ophthalmic surgery, by a system and instrument which continuously presents information to the surgeon/user during surgery as to the precise location, aim, and depth of the surgical laser and also as to surrounding features of the subject tissue, in three dimensions. It is also an object of the invention to track movements of the subject tissue during surgery, particularly critical in eye surgery where eye movements can be very rapid and involuntary. It is further an object of the invention to provide a safe means of first establishing a reproducible firing sequence positioned in a three dimensional space, and then firing the sequence at high repetition rates, thus obviating the time consuming need to repetitively inspect, aim, and shoot each shot before proceeding to the next target. Still another object is to provide a system applicable to non-medical fields wherein a laser beam is used to effect a precise operation on a target or series of targets subject to movement during the procedure. These and other objects, advantages, and features of the invention will be apparent from the following description of preferred embodiments, considered along with the accompanying drawings.

DESCRIPTION OF THE DRAWINGS

In FIG. 1 the work station is configured for ophthalmic surgery.

FIG. 2a is an enlarged perspective view of the control panel of the apparatus from FIG. 2.

FIG. 7 is a schematic view in perspective illustrating the off-axis projection of a Ronchi ruling onto a curved, warped or generally spherical surface such as that of the eye, and the on-axis viewing of that projected Ronchi ruling by a camera.

FIG. 8 is a schematic representation showing an image which might be seen by the camera in FIG. 7. The image shown corresponds to the interference pattern between the projected Ronchi ruling as distorted by the target and the reference ruling.

DESCRIPTION OF PREFERRED EMBODIMENTS

Figure 1:
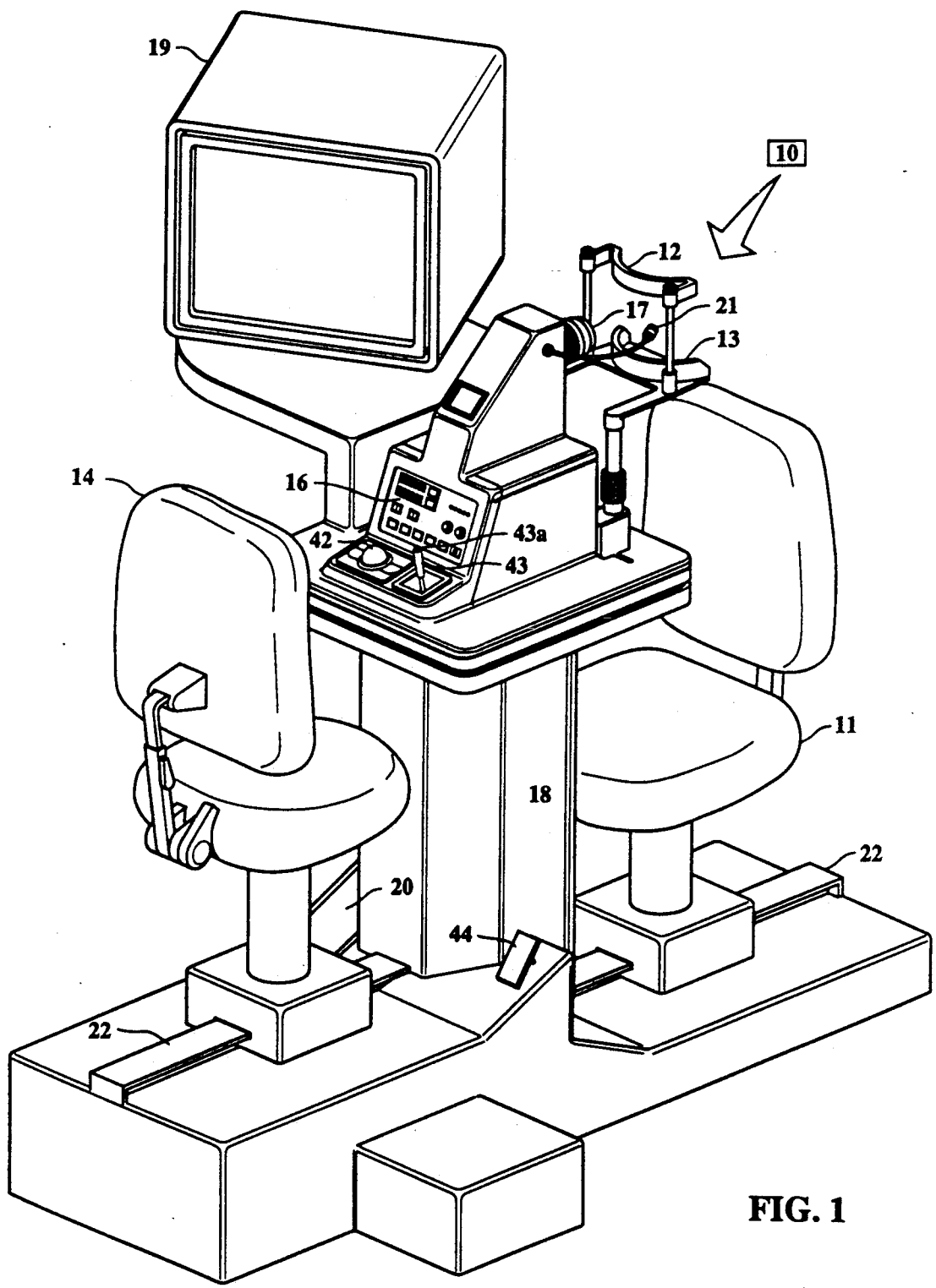
FIG. 1 is a perspective view showing an instrument or work station for performing precision laser surgery in accordance with the principles of the invention.
Figure 1A:
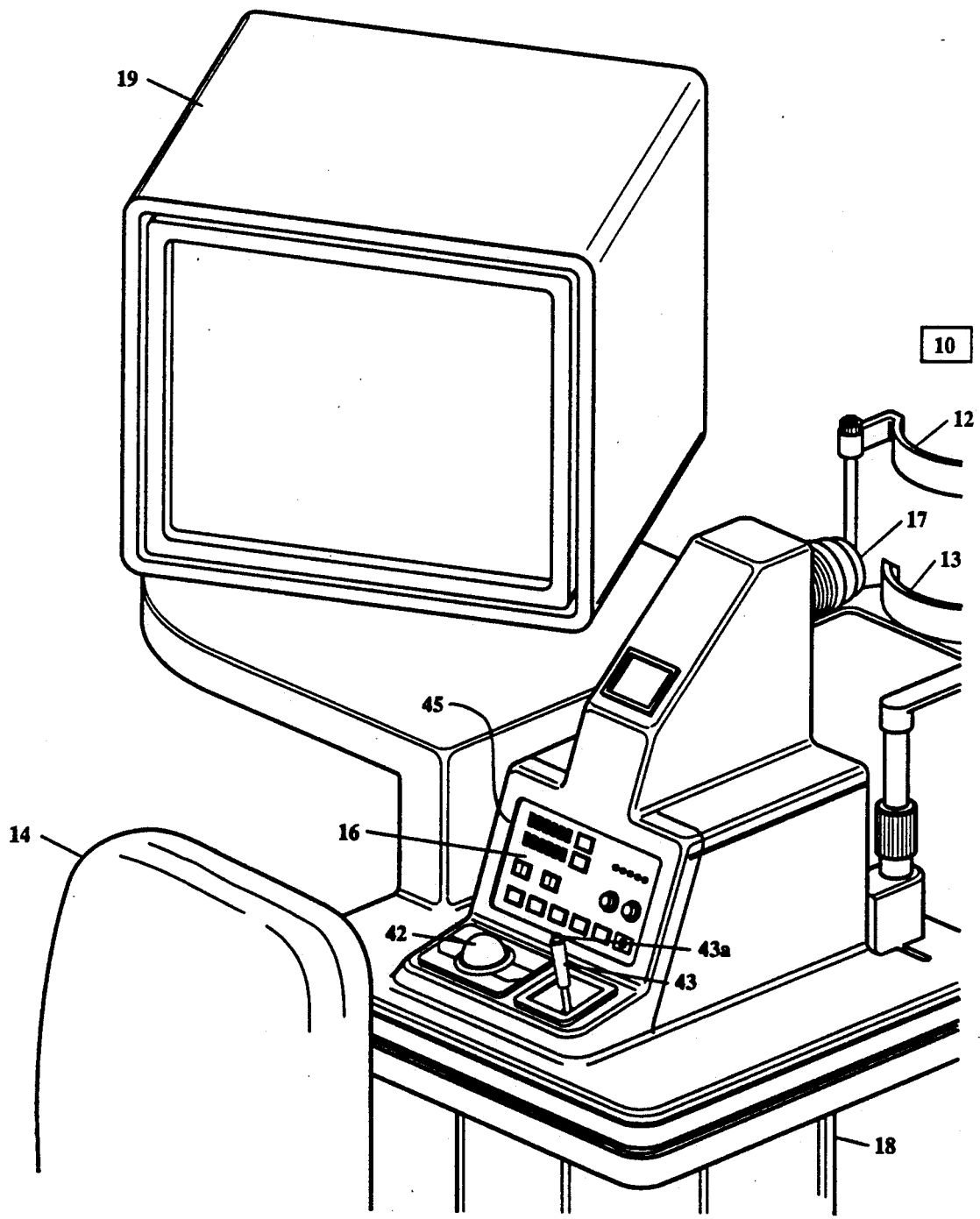
FIG. 1a is an enlarged perspective view showing a portion of the apparatus from FIG. 1.

In the drawings, FIG. 1 shows a precision laser surgery and diagnostic/analytical instrument 10 in accordance with the principles of the present invention, in the form of a work station. The work station 10 in this illustrated embodiment of the invention is intended for ophthalmic surgery, with the patient to be seated in a chair 11 with his forehead against a forehead rest 12 and his chin against a chin rest 13. The surgeon/user sits a chair 14.

Although the system, apparatus and method of the invention are illustrated and discussed with reference to ophthalmic surgery and diagnosis, it should be understood that the invention encompasses other types of medical diagnostic and surgical procedures, as well as non-medical operations (e.g. precision fabrication procedures using lasers and laser based communications procedures).

The instrument and system 10 of the invention further include controls 16 for a vision system and laser firing, enabling the surgeon/user to survey the topography and internal features of the tissue to be operated upon (the eye in the illustrated work station), and to precisely control the path of firing as well as the pattern of firing of a laser beam in three dimensions. As will be explained below, the surgeon may control the firing of the laser manually or with pre-programmed "templates" which can be superimposed over an image of the tissue being operated upon, and which enable an automatic tracing of a desired laser firing pattern based upon prior experience with similar surgical procedures.

The system can also include a final focussing lens or front lens element 17 (an element of an objective lens assembly, as explained below), through which certain images are taken and through which the laser beam is directed at the subject tissue. An illuminating light beam may also be projected at the tissue through the final lens 17. A central column 18 of the instrument 10 may contain the therapeutic laser, an illuminator, and surgical microscope, none of which is seen in FIG. 1.

The system also includes an appropriate form of display means, preferably a CRT video screen 19 as illustrated.

A foot pedal 20 may be provided for the surgeon, as a safety device which will both enable the laser triggering means when sufficient pressure is exerted on the foot pedal 20, or alternatively will immediately interrupt laser firing if foot pressure on the foot pedal 20 is released.

Also indicated in FIG. 1 is a light projector 21 or an appropriate projector for three dimensional mapping system directed at the tissue, e.g. the eye of the patient. In preferred embodiments of the invention, the light projector 21 projects a Ronchi ruling onto and into the eye, and images of the Ronchi on and in the eye are analyzed by a profilometer camera (not seen in FIG. 1) which also utilizes the final focussing lens 17, sharing a portion of the optical path of the surgical microscope, the therapeutic laser, and the illuminator.

As also indicated in FIG. 1, the seating 11 and 14 for the patient and the surgeon preferably is fully adjustable with tracks 22 for adjusting proximity to the apparatus and with full height and seat back adjustability. The forehead and chin rest 12, 13 is adjustable.

Figure 2:
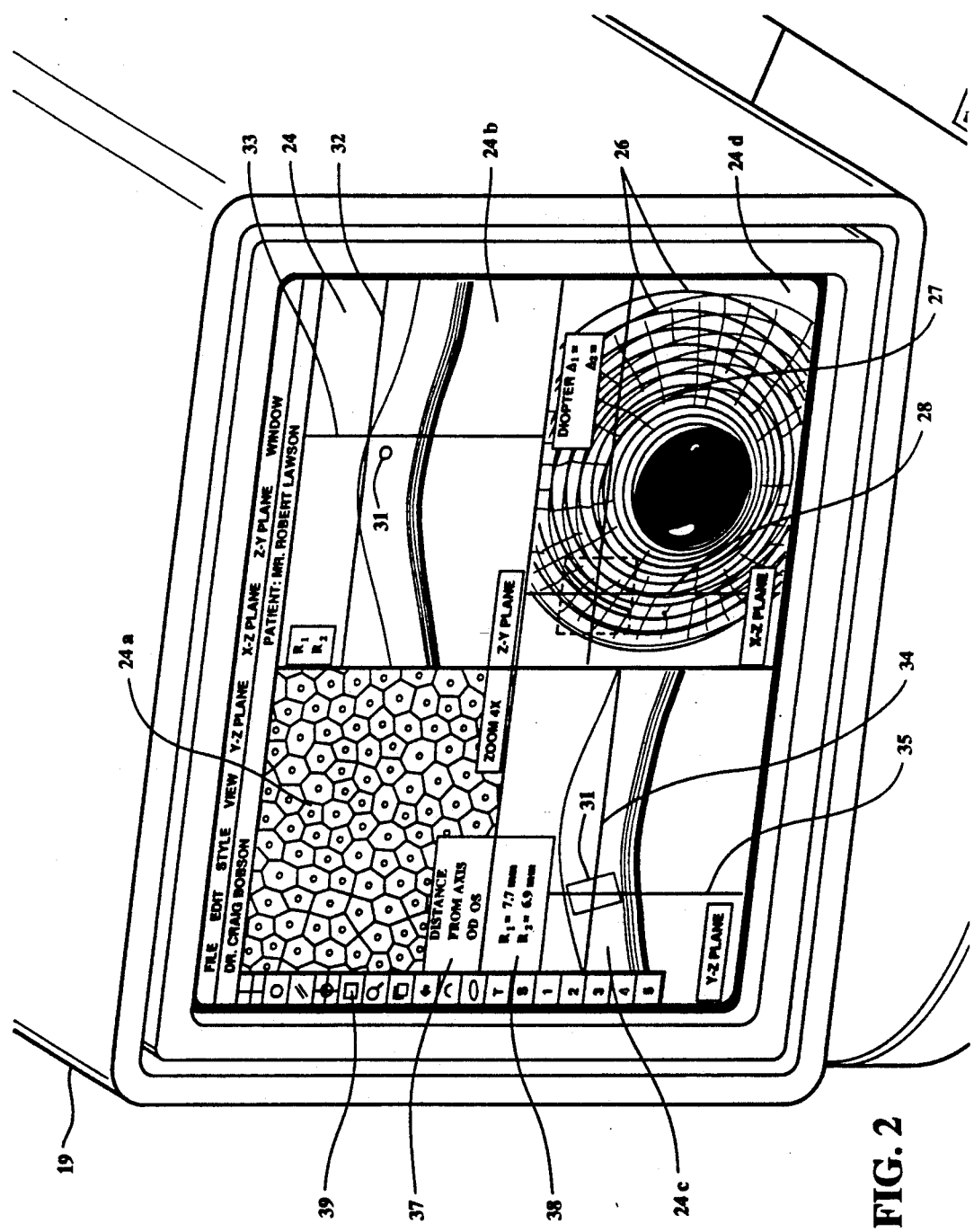
FIG. 2 is an enlarged plan view of a video screen showing an example of information which may be presented to the surgeon/user during the anterior segment ophthalmic surgical procedure.

FIG. 2 shows an example of what may be displayed on a screen 24 of the video monitor 19. The information on the screen 24 is intended to give the user a full range of information regarding the three dimensional structure and features of the particular tissues on which laser surgical procedures are to be performed. For example, the screen may be divided into four quadrants as illustrated. The upper left quadrant 24a may show the image from the video microscope. Thus, individual cell walls may appear in this quadrant as indicated, with relatively high resolution and contrast. These cell walls might be the cells at the inner surface of the cornea, or corneal endothelium. As explained further below, the surgical microscope preferably has a zoom adjustment, so that the magnification power as presented on the screen might vary from about 25× to 500×, as desired by the surgeon/user.

The lower right quadrant 24d of the screen, as illustrated in FIG. 2, can present an enlarged plan view of an area of the patient's tissue, preferably through the full field where the surgical therapeutic treatment is desired. In ophthalmic surgery, this field might comprise, for example, a field of greater dimensions than the cornea for anterior segment procedures, if the surgery is to be conducted in the cornea. For this type of surgery, the plan view or X-Y plane shown in the quadrant 24d may have contour plot with contour levels 26 superimposed concentrically over the image of the cornea. Crosshairs or crossed lines 27 and 28 identify for the surgeon the precise point at which the surgical therapeutic laser is currently directed. These crossed lines may also indicate the line cuts which define the axis for the cross sectional plane representations of the tissue shown in screen quadrants 24b and 24c in FIG. 2. Thus, the crosshairs or crossed lines 27 and 28 in the quadrant 24d indicate planes at which cross sectional representations in the quadrants 24b and 24c are taken. The upper right quadrant 24b shows a cross section along the X-Z plane, taken along the line 27. Similarly, the lower left quadrant 24c of the screen represents the Y-Z plane along the crossed line 28 shown in the quadrant 24d.

In accordance with the preferred embodiments of the invention, the cross sectional representations of the quadrant 24b and 24c are computer-generated images. In this illustration, the images are of the cornea of the eye with the epithelium surface and the endothelium surface, and the stroma located between the epithelium and the endothelium surfaces. In this example it is presumed that a surgical procedure is to be undertaken on an aberration, foreign body, or cluster of diseased tissues 31 indicated on the two cross sectional quadrants. Alternatively, if the optical properties of the cornea, which constitutes the main refractive power lens of the eye, are not to the satisfaction of the patient and surgeon, the surgical procedure may be undertaken to modify the refractive power of an otherwise healthy cornea.

As also indicated in FIG. 2, the cross sectional representations in the quadrants 24b and 24c also include intersecting lines 32, 33, and 34, 35 to indicate to the surgeon precisely where the laser is currently targeted and focused, even though it may not currently be firing.

As illustrated in the quadrant 24a and 24c on the left side, there may be an on-screen display of certain dimensions or locations. Thus, boxes or windows 37 and 38 may be generated on the video screen to show pertinent data relating to the tissue on which surgery is to be performed. In addition, there preferably are included some symbols on the screen such as in a vertical strip 39 shown on the left side of the screen in FIG. 2. These symbols comprise a menu of selections for the surgeon, preferably in a branching look-up table format. These will include the type of display desired for the screen quadrants 24b, 24c, and 24d; selection of templates indicating a pre-programmed pattern for the proposed surgical procedure, and other surgical parameters such as the laser pulse power level or the repetition rate of the laser beam, the beginning and ending diopter power of the corneal "lens", the shape of the lesions, modifications of the templates, creation of new templates, memory storage and retrieval of information, record keeping and access to patient history files, access to statistical information about the likely outcome of a proposed surgical procedure, a selection of which level within the eye information is desired for a given surgical procedure (e.g., the screens as shown in FIG. 2 for corneal surgery, or a different set of screens for cataract surgery, or yet a different set of screens for posterior eye segment procedures), and others. The selection from this menu can be made from a cursor which is preferably located in the strip 39 shown on the screen and which can be manipulated by a keyboard input or preferably (in order to obviate the risks of mis-keying on a keyboard) a traction ball such as a "ball mouse", for example the products referred to commercially by the trademark "Logimouse", such as shown at 42 in FIG. 1.

Regarding the use of pre-programmed templates of the surgical path to be followed, the surgeon has a number of options. He can take previous templates stored in memory and derived from other previous surgeries conducted by himself or by other surgeons. He can create a new template or modify an old template. This is a accomplished by superimposing a template on the screen over the ocular tissues. For example, a template can be drawn on the screen using MacPaint (a trademark of Apple Computer, Inc.) or another software based drawing system. The surgeon "draws" in three dimensions, using for example the three screen quadrant formats 24b, 24c, 24d shown in FIG. 2. Thus, the surgeon might first establish the pattern in the screen 24d in plan view, then define it in a first cross section on the screen quadrant 24c, then in another cross section in the screen quadrant 24b. Using the Logimouse, for example, the surgeon can locate the cursor on a point of a template path, click the logimouse, manipulate the Logimouse to move the point to a new location, then click it again to fix the new location of the point. Or, the surgeon can locate the cursor in the middle of a closed loop path on the screen, click the Logimouse and move the entire surgical path with movement of the Logimouse, to relocate the path in the same shape. Another click fixes the new location.

The surgeon can use an existing template, superimpose it on the images shown in FIG. 2, then modify the pattern as desired using an edit mode of the system. In this way, the surgeon can precisely define the path of laser-induced lesions to be generated in the ocular tissues, to obtain precisely the desired surgical therapy.

The controls 16 shown in FIG. 1 include a joystick 43 of the well known potentiometer type. This joystick 43 may be used by the surgeon to move the target position, i.e. the intersection of the crosshairs 27 and 28 in FIG. 2, to the left and right or up and down as seen in the quadrant 24d of FIG. 2. This is in respect to a plan view of the tissue, such as the eye in ophthalmic surgery. Thus, if the joystick is used to move the crosshair or section line 28 to the left in the quadrant 24d, in the X-Y plane as shown, this will similarly move the crosshair 33 to the left in the X-Z plane quadrant 24b immediately above. At the same time, the movement of the line 28 will have the effect of changing the cross sectional representation in the screen quadrant 24c, since the movement of that line also has the effect of changing the point at which the Y-Z plane cross section is taken. Similarly, if the horizontal-appearing crosshair 27 in the quadrant 24d is moved down as seen on the screen, for example, this will have the effect of moving the vertical crosshair in the quadrant 24c, and it will have the concurrent effect of showing a different cross sectional shape in the upper right quadrant 24b, which is the X-Z plane.

It is emphasized that the graphical, computer-generated representations shown in the three quadrants 24b, 24c, and 24d in FIG. 2 are merely examples of the way in which pertinent information can be presented to the physician. In fact, in the menu 39 at the left of the screen, there preferably are provided other types of presentations which can be selected by the physician.

The joystick controller 43 also contains the laser fire sequence command control 43a. A laser fire safety interlock foot pedal (not shown) requires two separate coordinated actions to commence a laser firing sequence.

The controls 16 shown in FIG. 1, for use by the surgeon user, also include numerical displays which provide actual position of the targeting mirrors, thus providing an alternate verification means of the correct functioning of the system, as well as a separate quantitative position indicator for manual override of several of the automated positioning features of the instrument. Other control and indicator features include the enabling (or disabling) of internal safety interrupts, a light emitting diode display which indicates when the tracking system and target acquisition system is operational and on-target, an LED which lights up when the system components have successfully been verified to be performing within system specification ranges, an LED indicating power is on, and a video display to assist in detecting location of a system malfunction. Additional safety LEDs acknowledge sufficient pressure on the laser fire safety interlock in a foot pedal, and whether the microprocessor generated template pattern is in control of the firing sequence.

Figure 3:
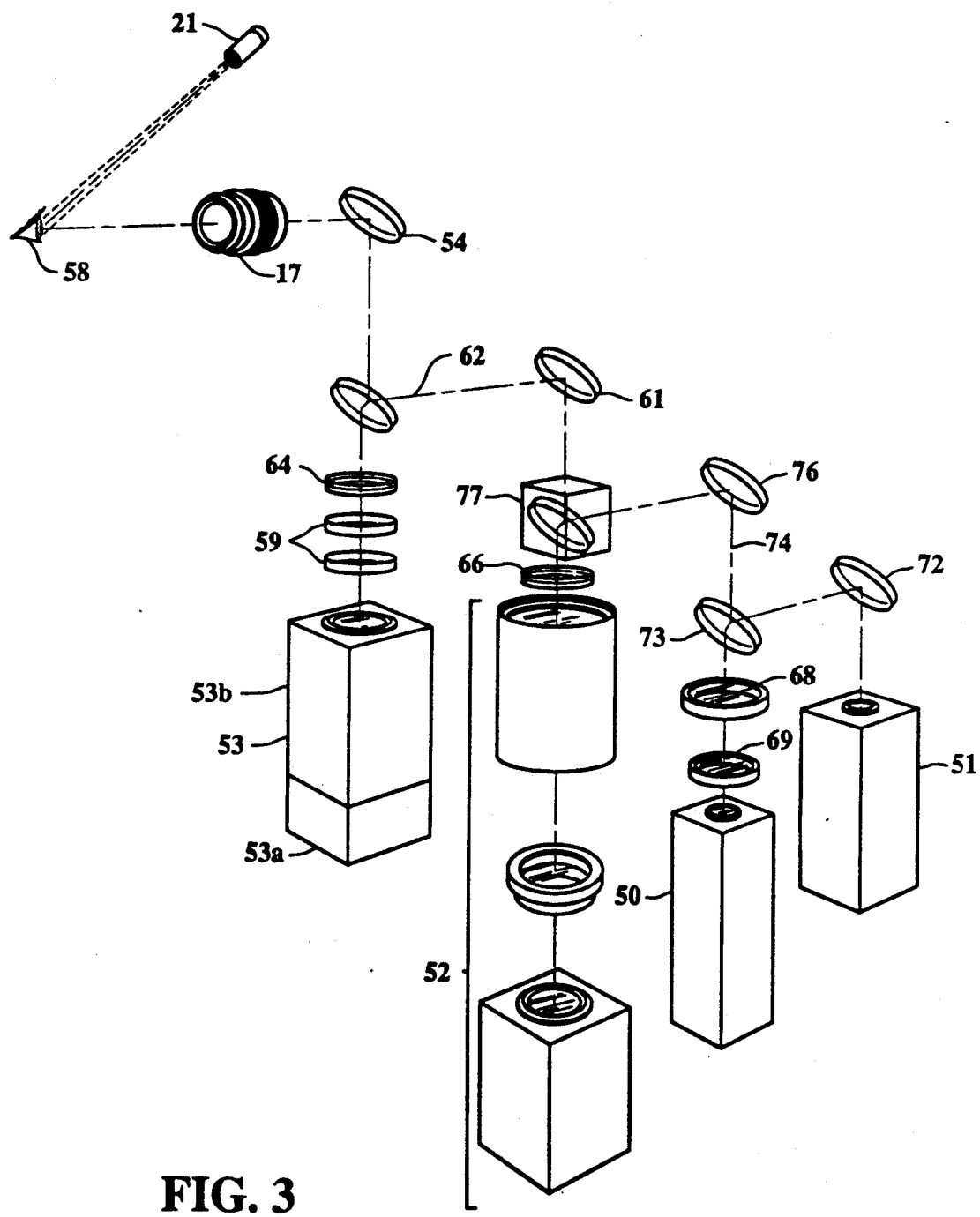
FIG. 3 is an exploded view in perspective, showing preferred optics and other components of the system of the invention.

FIG. 3 shows in exploded perspective view a preferred system of optics for the instrument of the invention. A surgical laser 50 is shown in a common optical path with an axial illuminator 51, a surgical microscope 52, shown exploded, and cameras 53a and 53b which have the functions of reading information from the tissue for computer generation of the cross sectional views shown in FIG. 2, and also tracking the tissue with movements of the patient, by finding and recognizing a given feature, through signals sent to the computer and programming, after that feature has moved to a new location. The two cameras are sometimes referred to collectively hereinas the tracking/profilometer camera 53. The camera 53b preferably includes a video camera, capable of taking images at a high rate of speed and is used for profiling and topographic imaging, low speed tracking, and image recognition. The camera 53a preferably contains dual linear, and preferably but not necessarily orthogonal, array detectors for high speed tracking.

By "common optical path" is meant, in the case of the tracking/profilometer camera 53 vis a vis the remaining optical elements shown to the right in FIG. 3, the camera 53 uses common optical elements with the other equipment, namely the tracking servo mirror 54 and the final focusing lens or front element lens 17. The tracking/profilometer camera 53 is intended to cover a certain field of view of the patient's tissue, such as an eye 58 (or a portion of an eye) shown in FIG. 3. Lenses 59 focus the image onto the faceplate of camera 53. It is not intended that the camera's image be moved laterally with respect to the tissue being viewed—only that it follow the tissue via the tracking servo mirror 54. The tracking servo mirror 54, which may be controlled by a piezo-electric (or similar) actuator, is shifted in its aim about X and Y axes in response to movements of the patient's tissue, so that the center axis of view of camera 53 always returns to the same point on the tissue. Similarly, the focusing lens 17 is adjusted as to focus, along a Z axis, in response to shifts in the depth of the subject tissue feature, so that the system always returns to a focus on the desired depth point in the tissue.

As indicated in FIG. 3, the distance of the patient's eye 58 from the final focussing lens 17 must be an appreciable distance, one great enough to allow the patient to feel comfortable. For this purpose, a distance of about 50 mm is considered minimum. It is preferred, however, that a more considerable distance be employed, at least about 100 mm.

The optical elements to the right in FIG. 3, i.e. the surgical microscope 52, the therapeutic laser 50, and the illuminator 51, all share the same optical path in being reflected off the tracking servo mirror 54 and passing coaxially (for the case of the surgical microscope subassembly and therapeutic laser subassembly) through the front element lens 17, but the axis along which these elements act is not necessarily coaxial with the axis of view of the camera 53. This is because of a directional positioning mirror 61 which is outside the optical path of the camera 53 but is within the optical path of the remaining elements, i.e. the surgical microscope 52, the laser 50, and the illuminator 51. The positioning mirror 61 is steerable under the control of the surgeon/user. The mirror 61 is adjustable about X and Y axes, and it therefore lets the physician select different locations for firing the laser within the field of view of the camera 53. Thus, an axis 62 of the three elements 52, 50 and 51 to the right in FIG. 3 will only be coincident with the axis of view of the tracking camera 53 when the surgeon aims the laser directly at the center of the field of view of the camera 53. In other instances they will share the same "optical path" via elements 54 and 17, but they will not be on identical axes.

The function of the positioning mirror 61 is better understood with reference to FIGS. 1 and 2, as well as FIG. 3. When the physician moves the joystick 43, this has the effect of moving the crosshairs shown in the computer-generated screen quadrants shown in FIG. 2, and of shifting the cross sectional image representations shown in the quadrants 24b and 24c. At the same time, the movement of the joystick shifts the orientation of the directional positioning mirror 61 to the same extent, which has the effect of (a) moving the surgical microscope image in the screen quadrant 24a to the left or right or up or down; (b) moving the actual aim of the therapeutic laser beam from the laser 50, which is precisely coaxial along the axis 62 with the surgical microscope, to a real aiming point which is coincident with the computer-generated aiming points shown in the screen quadrants 24b, 24c, and 24d; and (c) similarly changing the aim of the illuminator 51, which provides light for imaging by the surgical microscope 52.

The therapeutic laser 50 may be a frequency multiplied solid state laser (Nd:YAG, Nd:YLF, Erbium or others) which may be either flash lamp or diode pumped, or an argon, argon pumped dye, excimer, excimer pumped dye, nitrogen, nitrogen pumped dye, or any of a host of different lasers, or combinations thereof, currently available or in development. The present invention can be used with any laser by specifying different coatings where necessary for the optical surfaces. A quartz and magnesium fluoride focusing element is available as the element 17 to accommodate ultraviolet lasers. The present invention is not laser specific, but is intended as a surgical instrument intended for utilizing any therapeutic laser more efficaciously. The laser 50 preferably produces a pulsed beam which is controllable as to the level of energy per pulse, pulse peak power, and repetition rate.

Beam expander lenses 68, 69 preferably are positioned just downstream of the laser 50 and adjusted so as to expand the diameter of the laser pulse emerging from the laser cavity and collimate it so that a parallel but expanded beam of light emerges from the lens 68. The expanded, collimated beam arrives incident upon the final lens 17, and the expanded beam substantially fills the lens. Thus, a large-diameter beam is focused by the lens 17, so that only at the point of focus within the eye is the diffraction limited pulsed laser beam effective to generate the desired therapeutic lesions in the eye.

As illustrated in the schematic, exploded view of FIG. 3, the illuminator light beam first is reflected off a mirror 72, then off the reflective surface of a beam splitter mirror 73, to join substantially coaxially with the path of the laser beam along the beam axis 74. Both beams are then reflected off a mirror 76 and off a reflective surface in a polarizing beam splitter 77. This, along with polarizer 66, effectively prevents internal back reflections of the laser pulses from the optics of the system from damaging or overwhelming the sensitive video microscope camera. The illumination beam and the laser beam then join the common axis 62 with the axis of view of the video microscope 52, as illustrated.

As mentioned above, the surgical microscope 52 has zoom optics for adjustable magnification at the screen in the range of about 25× to 500×, for example. This enables the surgeon to view a very narrow field, e.g. tens of microns in width, or a much wider field, at lesser magnification. This is useful in enabling the surgeon to assure himself that he is aimed at and focused at a particular desired region. Zooming can be effected through use of the branching look-up table 39 shown in FIG. 2, with the ball mouse or trackball assembly 42 (see FIG. 1) controlling the selections by the surgeon.

The surgical microscope 52 preferably comprises an intensified video camera, for example a silicon intensified target (SIT) tube camera. Alternatively it can be a conventional video camera in combination with a microchannel plate intensifier. In either event the camera's sensitivity preferably is about 1000 times that of a normal video camera, enabling the system to look at weakly scattered light and targets poorly illuminated for the desired levels of high magnification at large working distances.

The final focusing lens 17 shown in FIGS. 1 and 3 is controlled automatically by the instrument as well as being controlled by the surgeon via the joystick 43. As described above, when the computer and programming sense, through inputs of the tracking and profilometer camera 53, that the subject tissue has moved and when the new location has been confirmed, the tissue may be at a different depth from the lens 17, as well as at a different lateral position in the field of view. This necessitates a change in focus of the lens 17, and this is effected automatically under control of the computer. The tracking and profilometer camera 53 has optics which give it a wide depth of field, so that features can be recognized even at different depths, before focus is adjusted. Thus, these features can be tracked while still in acceptable focus, and the final lens 17 can then be adjusted accordingly, to center the focus of the system at the new location. This is preferably accomplished via the profilometer camera 53b at its frame rate, but not by the much faster tracking camera 53a, as explained further below.

The surgeon often desires to change the depth at which the surgical microscope 52 is focused (the upper left quadrant 24a in FIG. 2 shows this video display), and simultaneously of the surgical laser 50. This is accomplished by rotation of the joystick 43 in one direction or the other, to focus the system more deeply or more shallowly, via the lens 17. This of course has an effect on the focal point of the tracking detector and profilometer camera 53 as well. It will change the center of focus of the profilometer and it will move the horizontal crosshairs down in screen quadrants 24b and 24c, but the depth of field of the profilometer camera 53b is broad enough that the images will still be obtained. The surgeon's adjustments of the focus of the final lens 17 are superimposed on top of the automatic adjustments effected by the tracking system, and net focus changes are carried out by the system.

In one embodiment of the invention the tracking detector consists of high speed linear array detectors in two orthogonal directions and an array processor such that updated position information is fed to the tracking mirror at frequencies substantially higher that the repetition rate of the laser or the frame rate of the imaging cameras. The response time of the tracking detector and processor will be substantially under one millisecond.

The final focussing lens 17 forms a part of a split microscope objective lens assembly of the system of the invention. The lens 17 comprises the front element of the objective lens assembly, while the rear element of the objective lens comprises one of the elements of the tracking detector and profilometer camera 53 or of the surgical microscope 52 or of the laser 50 optics or of the illumination source 51. This is shown schematically in FIG. 10, where the back element of the objective lens assembly is indicated at 70. The image plane of this back element of the objective lens can represent an element of any of the components mentioned above, such as the intermediate focal plane of the surgical microscope, the face plate of the profilometer camera, the face plate of the tracking detector array, or the condenser of the illuminator. Thus, the front element of the objective lens is common to a variety of optical assemblies. The collimated laser beam is inserted via a beam splitter between the objective elements, hence the front element of the objective lens is likewise common to the laser beam assembly.

Figure 10:
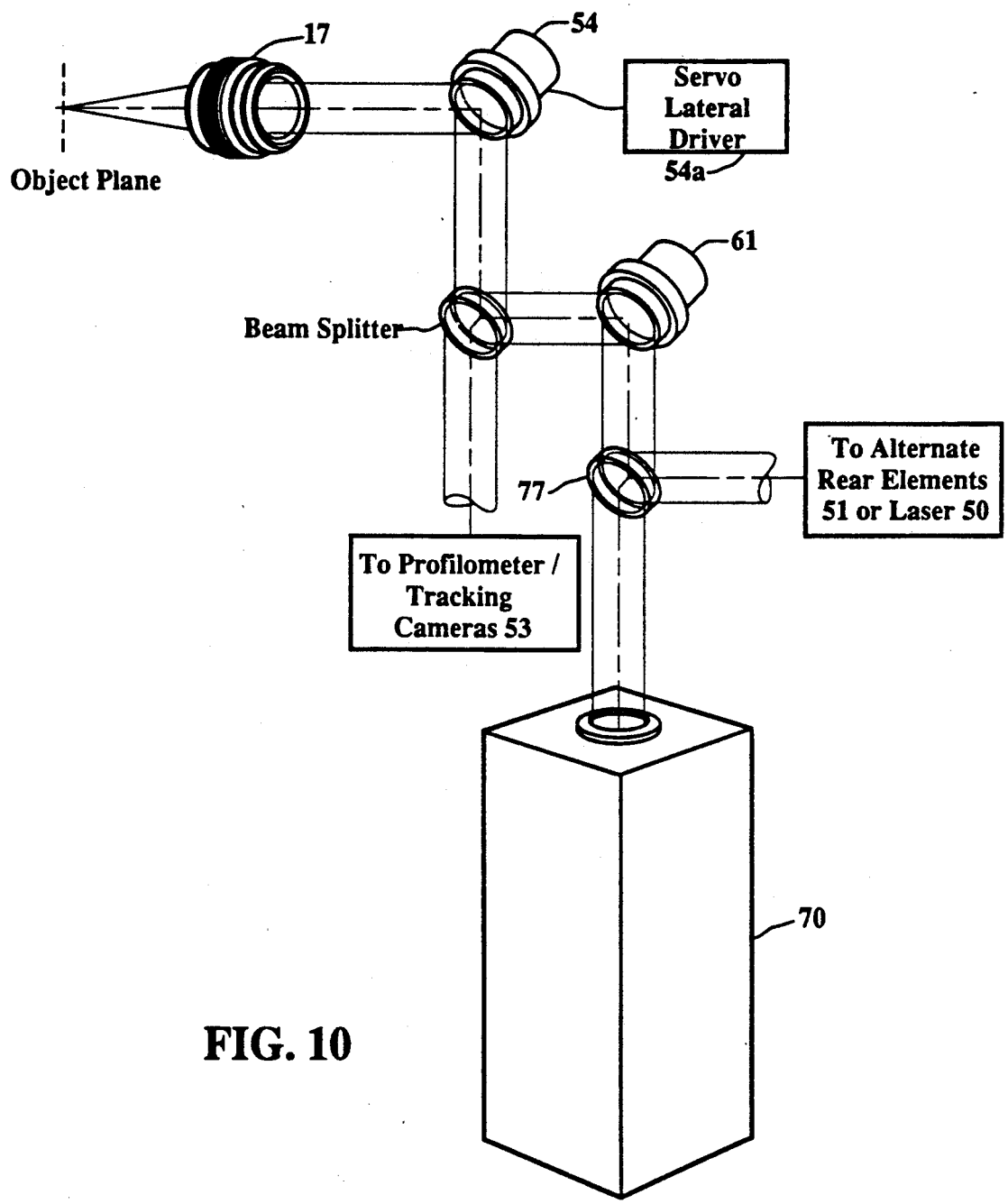
FIG. 10 is a schematic representation of an objective lens assembly forming a part of the system of the invention.

An important feature of the optics of the system of the invention is that the servo tracking mirror 54 actually is positioned inside the objective lens assembly, as illustrated schematically in FIG. 10. (The final element has been designed to have sufficient field to accommodate the small misalignments caused by the tracking mirror.) This enables the system to achieve rapid tracking of ocular features (or other tissue features) in an efficient and relatively simple assembly, without moving an entire objective lens in following the sometimes rapidly moving features.

Tracking a target moving randomly at speeds greater than 20 millimeters per second requires the ability to redirect the imaging axis very quickly. Large moving masses must be avoided for the rapid tracking. The moving mass can be limited in the present invention to a very thin mirror 54 (e.g. a mirror of a few mm thickness with a flatness of a wavelength or better). The very thin, lightweight mirror is capable of achieving very rapid tracking on rapidly moving objects by quick changes of the aiming direction of the mirror 54, along X and Y axes. This may be accomplished using a piezoelectric or similarly driven servo mirror, a type of mirror control known in the optical systems industry, albeit not in the ophthalmic community.

FIG. 10 illustrates schematically that the thin, lightweight mirror is mounted to a high speed servo driver to form the servo mirror assembly 54. An electrical lead is shown leading to the servo interface driver 54a.

Therefore, with the preferred servo mirror assembly of the invention, mounted within the objective lens assembly, the mirror 54 redirects images which pass through the final focussing lens 17, the front element of the objective lens assembly. The lens 17 has a sufficiently large working field to accommodate the image variation off-axis in the lens.

When the surgeon is ready to fire the laser, he does so by holding down a fire control button 43a shown in FIG. 1. If the surgeon has activated a pre-selected template, the pushing of the button may in this case be made effective to activate the template to carry out the desired surgery. Another touch of the button 43a will then cancel or interrupt the path of surgery. In all cases above, the foot pedal interlock 20 must be depressed, as an added safety control feature, for laser firing to occur.

Figure 4:
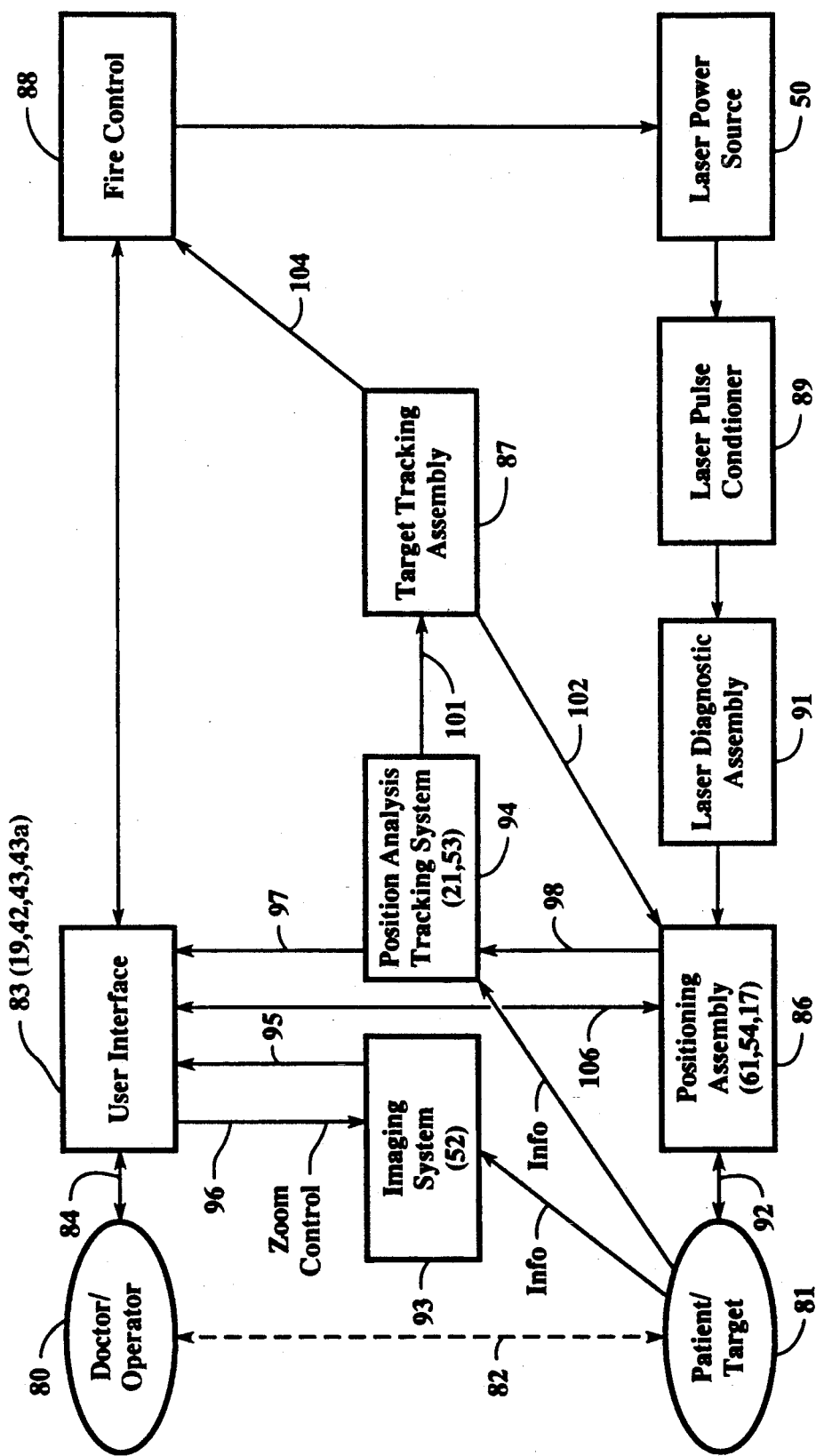
FIG. 4 is a block diagram relating to the system of the invention.

FIG. 4 is a functional block diagram showing principal components of the precision laser surgery system of the invention. The surgeon user is indicated at 80, with the patient/target indicated at 81. Interaction between the surgeon and the patient is indicated by a dotted line 82.

This interaction is mostly indirect, via the instrument and system of the invention. The dashed line 82 represents the surgeon's indirectly carrying out the surgical procedures on the patient, and the patient's tissue indirectly feeding back information and data, through the instrument, to the surgeon, via the video display 19.

In this embodiment of the invention, the surgeon/user is provided the option of both direct observation and tactile manipulation of the patient/target because of the compactness of the design of the instrument and the large desired working distance between the final focusing element 17 and the patient 58.

The user interface of the system is indicated at 83. The surgeon user inputs instructions and commands to the user interface 83 and the user interface feeds back information to the user, principally via the video screen 19. This is indicated by a line 84. The user interface 83 comprises for the most part the video screen 19, the mouse or trackball assembly 42 for making selections, the joystick 43, the fire control button 43a and various buttons and numerical displays indicated in FIG. 1 in front of the surgeon user. Aside from the safety feature indicators discussed previously, a traction ball (the "Logimouse" 42 shown in FIG. 1 but not shown in FIG. 4) is placed near the joy stick to enable the surgeon/user to control and select from among the various software options available. Rotation of the traction ball (a commercially available "mouse" alternative such as Logimouse) controls the position on the video screen. A button next to the ball enables special features on the screen and allows the user to superimpose on the video generated corneal images the proposed therapy. In the present invention, computer graphics software packages such as MacPaint and MacDraw form a portion of the basis for providing the surgeon/user access to defining surgical templates. Other buttons allow the surgeon/user to switch from selecting previously defined templates, to modifying or creating templates.

With the user interface, the surgeon is able to make selections as to types of surgery or templates to be used in the surgery, to view different portions of the tissue, to aim the laser, including the depth at which the laser fires, and to fire the laser or execute a pre-programmed sequence of firings. It also enables the surgeon user to interrupt the procedure at any time. FIG. 4 shows separate blocks 86, 87 and 88 for the positioning assembly, the target tracking assembly and the fire control, all indicated as being under control of the surgeon user by lines from the user interface with arrowheads directed at these blocks 86, 87 and 88. Thus, the block 88 indicates an internal fire control activated by the push of the button 43a shown in FIG. 1, and this in turn activates the laser power source, i.e. the surgical laser 50. The laser power source 50 is connected to a laser pulse conditioner indicated by the block 89, which produces a pulsed laser beam of the desired shape. The beam passes through a laser diagnostic assembly 91, which serves the purpose of monitoring the continued pulse-to-pulse performance of the laser to insure it is performing to specification. The beam is then indicated as being passed through the positioning assembly 86 (not all optical components are indicated in FIG. 4). The positioning assembly 86 includes the laser beam directional positioning mirror 61, which is under the control of the surgeon via the joystick 43 as discussed above. A dashed line 92 indicates the laser beam's action on the target, i.e. the patient.

As represented in FIG. 4, the positioning assembly 86 also includes the automatically controlled tracking servo mirror 54 (see FIG. 3), as well as the front objective element 17. The positioning assembly 86 is shown in FIG. 4 as receiving control instructions from the target tracking assembly 87, and this control amounts to control of the servo mirror 54 to adjust the mirror whenever the patient's target tissue moves.

The patient/target 81 is shown as sending information to an imaging system 93 and to a position analysis tracking system 94. As thus represented, the imaging system 93 comprises the surgical microscope 52, which presents the video image exemplified in the upper left quadrant in FIG. 2. An arrow 95 indicates transmission of the video information to the video display, forming a part of the user interface 83. A control arrow 96 between the user interface and the imaging system 93 indicates that the surgeon may control the magnification of the surgical microscope, as discussed above.

The position analysis tracking system 94 includes the tracking/profilometer camera 53 (the camera/detectors 53a and 53b) and, in a preferred embodiment, the Ronchi ruling light projector 21 shown in FIG. 1. This subsystem 94 receives images from the patient/target 81, as discussed above, for detecting and following any movement of the patient's tissue. An information arrow 97 is shown between the position analysis tracking system 94 and the user interface 83, indicating stabilization of the video images by the subsystem 94, as well as the feeding of information to the display for the profilometer images. The subsystem 94 includes the microprocessor and programming which are able to analyze images taken by the profilometer/tracking camera/detectors 53 and to determine from the camera/detector data when features have moved and to relocate those features and calculate new coordinates for mirror position. It includes the slow tracking profilometer camera 53b and the fast tracking detector 53a, as well as slow and fast logic loops. Some of these functions are described further with reference to FIGS. 5A through 9.

In the claims, the terms "position analysis means", "target tracking means", and "tracking positioning means" are used. These terms correspond generally but not precisely to the blocks 94, 87, and 86 respectively in FIG. 4. There is some overlap in the terms, as further explained below.

FIG. 4 shows an information or control arrow 98 leading from the positioning assembly 86 to the position analysis tracking system 94. This represents feedback from the mirror assemblies as to their actual position. It also includes confirmation that the mirror was physically moved, i.e. that the instruction to the mirror resulted, where indicated, in a physical displacement. If this move does not occur, the system loops back to the target tracking assembly 87 which sends a signal 104 to disable the laser firing.

The position analysis tracking system 94 is shown sending information or commands to the target tracking assembly 87, by a control arrow 101. This indicates that the subsystem 94, after analyzing the images and determining that a feature has moved, sends information or instructions to the target tracking assembly (also embodied in the computer programming). The information or instructions can comprise new coordinates for the mirror position 54. The target tracking assembly 87 translates the new coordinates into instructions for the mirror drivers (arrow 102 to the positioning assembly 86), i.e. the servo mirror 54. This instruction includes coordinate transform information and instructions for the servo mirror 54 to turn to a new angle which will again be centered on the same features. The target tracking assembly 87 also sends commands regarding the focus, and thus adjusts the focus of the final focussing lens 17 as discussed above, and the lens 17 should be considered as forming a part of the positioning assembly 86 (preferably in a slow tracking loop as discussed below).

Of course, the final focussing lens also forms a part of the imaging system 93, in the sense that the surgical microscope receives light on a path which passes through this lens 17, and the focus of the imaging is adjustable by the surgeon/user.

An important control arrow 104 is shown in FIG. 4, relating to a preferred safety feature discussed above. The target tracking assembly 87, if unable to track the moved feature to a new location within the time allotted (which may be 1/30 second or faster in one embodiment or 1 millisecond in another), will send an instruction to the internal fire control 88, to abort firing of the laser.

A double-ended arrow 106 in FIG. 4 between the user interface and the positioning assembly indicates control by the physician, via the joystick 83, of the directional positioning mirror 61, as discussed previously; and also feedback from the positioning assembly to the user interface. Such feedback would include the actual movement of the crosshairs indicating position, as described with respect to FIG. 2, as well as changes in the cross-sectional shapes as the cross-sectional cutting planes are moved by the physician, if these image formats are used. This line also carries internal encoders indicating that instructions have been carried out.

It should be understood that the system of the invention is useful to the surgeon as a diagnostic and analytical tool, aside from its uses in actual surgery. The system provides for the doctor highly stabilized images of the patient's tissue, particularly the ocular tissue, not achievable with instruments prior to this invention. The doctor is given a real-time display of the tissues, with tracking and stabilization in real time. The invention therefore gives the doctor a very important tool in analysis and diagnosis of a patient's condition, and the invention should be understood to encompass the system as described even without the surgical laser beam itself. The system, with its computer-generated images on the display screen as well as direct video microscopic images displays of the patient/target, gives the doctor a means of visualizing the eye condition, as a replacement for the doctor's directly looking at the target tissues.

Figure 5:
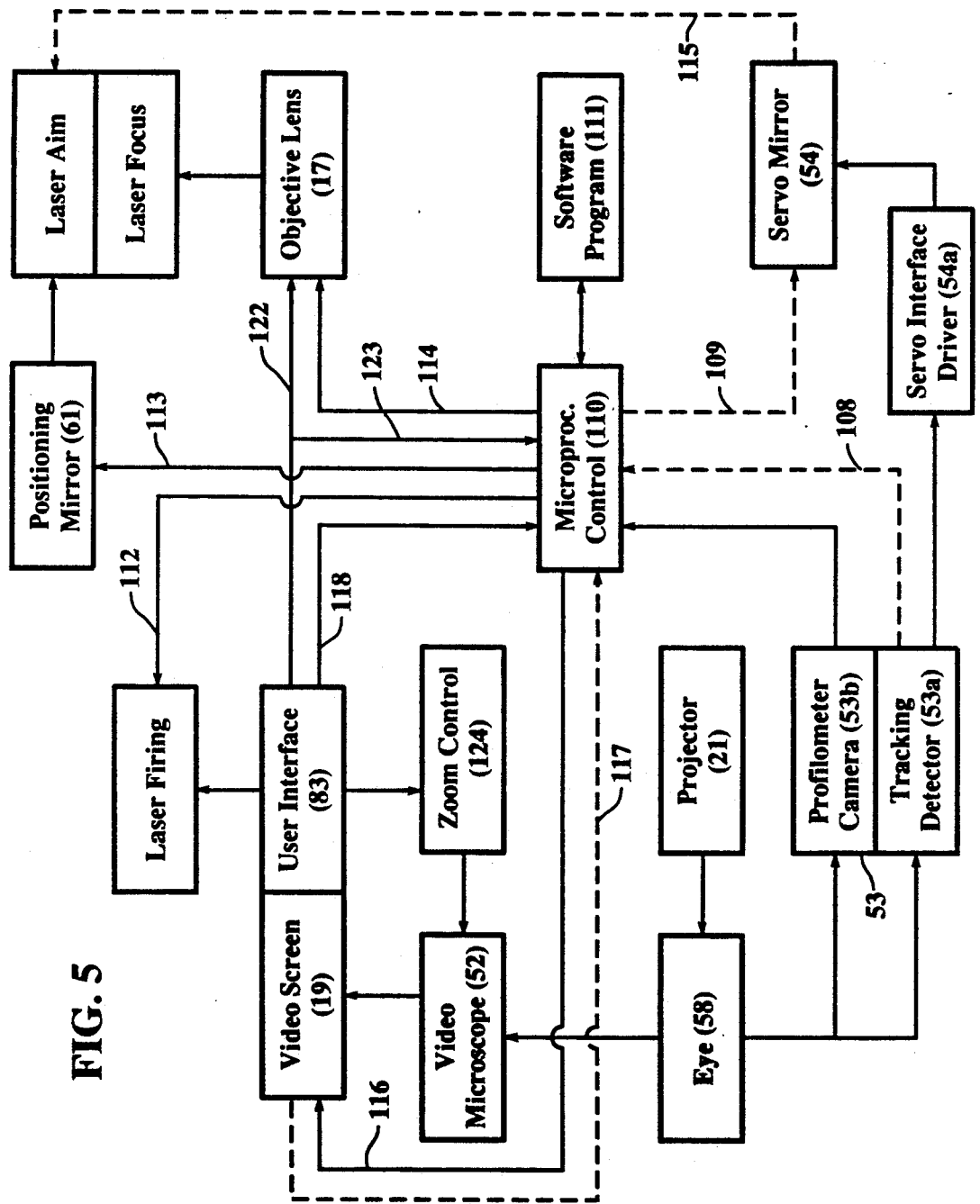
FIG. 5 is a more detailed block diagram showing control and information flow among various optical components and user interface elements of the system of the invention.

FIG. 5 is a block diagram showing in greater detail some of the individual control and informational feedback functions regarding the components of the system of the invention.

FIG. 5 shows a microprocessor or central processing unit in a block 110, and programming 111 communicating with the microprocessor. As indicated, the user interface has some communication with the microprocessor 110 and some controls which do not involve the microprocessor. For example, if the surgeon wishes to select a template for surgery, or merely to change the display on the video screen (FIG. 2) for the purpose of selecting a different type of presentation, or for imposing a different surgical path on the screen, etc., these communications are with the processor, which controls the computer-generated images on the screen as well as controlling many other functions in the system.

In one embodiment of the invention, the microprocessor 110 also controls the tracking mirror or servo mirror 54, as indicated. The microprocessor controls the mirror in response to input from the tracking/profilometer camera 53 (the cameras 53a and 53b) in conjunction with the program software 111. Thus, once the tracking camera 53a inputs signals to the microprocessor (via dashed line 108) which indicate that the subject tissue has undergone movement, the microprocessor handles the position analysis and the low speed target tracking (mirror instruction) as indicated in the blocks 94 and 87 in FIG. 4 and outputs a signal in response to the results of the tracking, to the tracking mirror 54 (dashed line 109 in FIG. 5).

However, in a preferred embodiment of the invention, the fast tracking detectors 53a in camera 53 will communicate directly with a servo interface and drivers 54a which directly control the servo mirror 54. The unit 54a can be a dedicated microprocessor or other logic unit having the capability of carrying out the logic sequence needed for pattern recognition, coordinate transform analysis and generating instructions to the mirror drivers to appropriately adjust the mirror 54. In FIG. 5, the servo interface driver includes some of the logic functions of the block 94 in FIG. 4, as well as the functions of the block 87.

This preferred embodiment of the invention, along with more responsive servo mirror designs, allows a much faster closed loop tracking response time than via the microprocessor 110.

The tracking mirror thus rotates to the appropriate new position. This is confirmed in the microprocessor by the location of the image itself, after the mirror has completed its instructed motion. However, as mentioned above, if the microprocessor and programming determine that the feature has not been recognized in the next scan of the target region (or within a preselected number of said subsequent scans, depending on the desired tracking rate as determined by the requirements of a given surgical procedure), the microprocessor will immediately interrupt laser firing (as indicated on a control line 112) and it will also interrupt the execution of the template program, vis a vis the movement of the position mirror 61 which steers the path of laser. This is indicated on control line 113 in FIG. 5. The template program will generally also involve adjustments in the focus of the final lens element 17, and this is indicated by the control line 114 in FIG. 5. The interrupt preferably lasts only until the feature is recovered via the slow tracking loop (discussed further below), if in fact the feature is recovered.

A dashed control 115 from the servo tracking mirror 54 to the laser aim block indicates that the laser aim is steered along with the tracking (see FIG. 4), but as the laser and surgical microscope lines of sight are coaxial, the field of tissue being viewed and the laser are always tracked as one.

The microprocessor sends signals to the video screen (along control line 116), the content of these signals relating particularly to the computer-generated topographical images, examples of which are shown in the screen quadrants 24b, 24c and 24d in FIG. 2. The microprocessor also controls the display of the branching look-up table 39 shown in FIG. 2, as well as other displays on the screen other than the video microscope image itself. If the video screen and the microprocessor comprise a "touch screen" system as mentioned above, then the control line 116 also relates to this feature, and a further control line 117 is indicated as a dashed line in FIG. 5 from the video display 19 to the microprocessor, representing the touch screen functions.

A control line 118 from the user interface to the microprocessor indicates the surgeon user's selections made by input controls other than touch screen. The control line 118 also indicates another user input to the microprocessor 110 active when the user steers the field of vision and the aim of the laser. Such deliberate control by the surgeon will indirectly control the positioning mirror via the microprocessor, along the control lines 118 and 113. Its signals to the microprocessor are also used by the microprocessor to adjust the computer-generated images accordingly, reflecting precisely the change in aim selected by the physician and using the information from the profilometer camera 53b.

FIG. 5 shows a similar control situation with respect to the surgeon's control of the depth to which the laser is focused i.e. via the final focussing lens 17. When the surgeon executes a change in the focus of the lens 17, as indicated along a control line 122 in FIG. 5, a simultaneous signal representative of the change is sent to the microprocessor, along the control line 123.

FIG. 5 indicates that the surgeon user has direct control of the zoom feature to adjust the magnification of the surgical microscope, indicated in the block 124.

As indicated earlier, there are two separate subassemblies which compose the preferred embodiment of the tracking subassembly. These comprise a relatively slower system or tracking loop operating at or near maximum video frame rates (usually 30 hertz) and a fast system or tracking loop operating faster than the attainable video rate. The slower system utilizes the image from the profilometer camera 53b and analyzes essentially frame by frame the shift of salient features in the image. The positional shifts, as computed by the processor 110, are utilized to reposition the servo mirror 54. This system is comparatively slow but has the advantage of being able to find an absolute position on the target even after a temporary loss of tracking. For example, if a surgical procedure is in process and an obstacle, such as a blinking eyelid in many ophthalmic procedures, interposes the tracking image such that the procedure is interrupted or temporarily aborted, this slower system will automatically store in memory the last position in the firing sequence so that once the target is again reacquired, the exact location of the next point in the firing sequence can be determined automatically and the servo mirror be repositioned accordingly.

The faster system uses an orthogonal pair of linear detector arrays in a high magnification focal plane. As indicated in FIG. 5, a dedicated processor or simpler servo interface driver 54a analyzes the phase shift of, for example, specific Fourier modes of the signal in successive readouts of the arrays. The linear array detectors and dedicated processor or servo-driver are extremely fast (e.g., greater than 10 KHZ for complete array readout); thus, the faster system is limited in speed only by the response time of the servo mirror and drive 54. However, because of its limited data collection and analysis, the faster system is not designed to recover an absolute location after a transient tracking loss.

The servo mirror 54, in an embodiment of the invention, may utilize, for example, a motor driven mount for the slower tracking system and a piezo-electric driven mirror for the fast system.

Figure 5A:
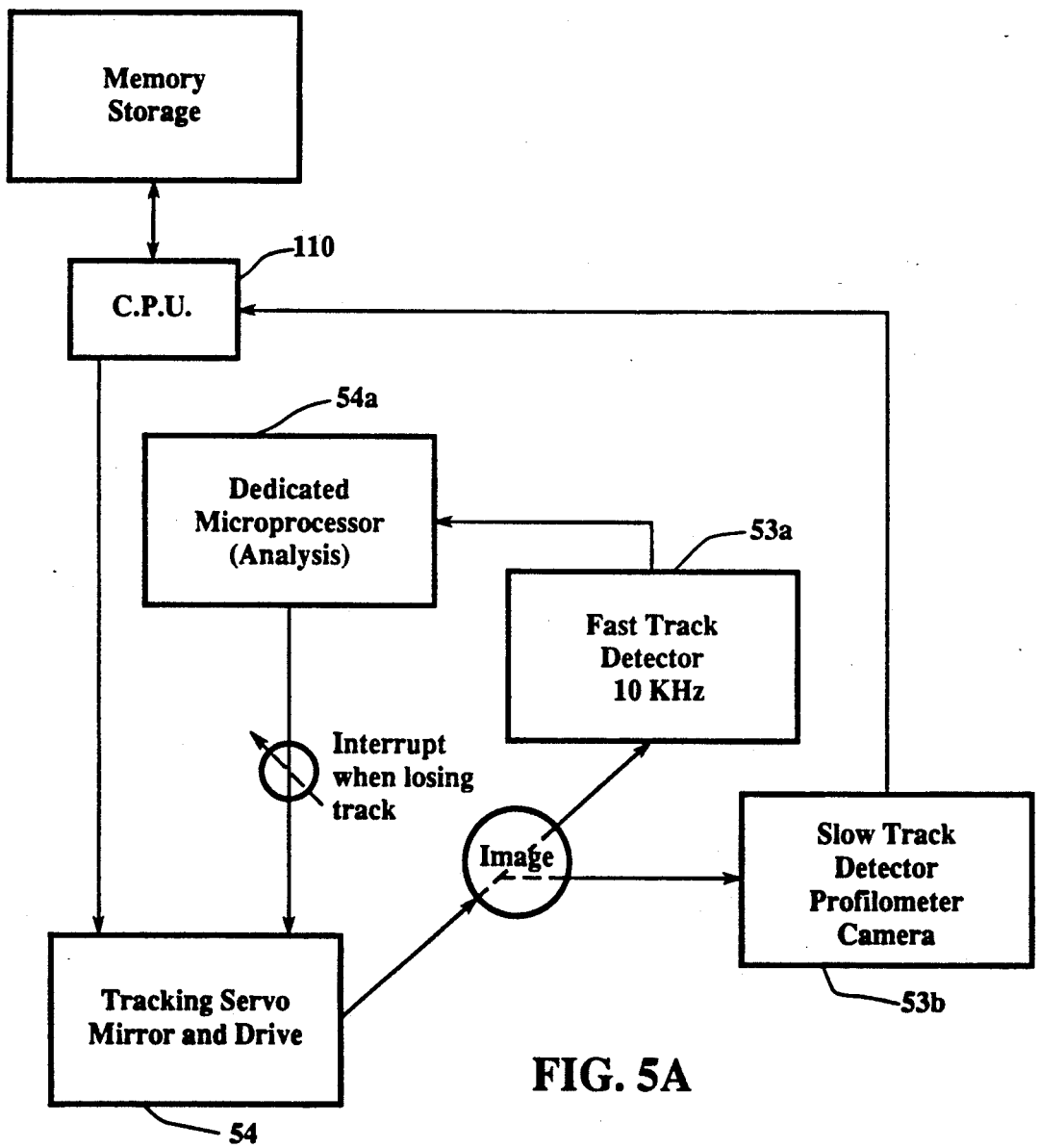
FIG. 5A is a block diagram indicating the interplay of the two separate but cooperating tracking methods, the fast and slow tracking loops.

FIG. 5A is a block diagram specifically showing functions of the tracking system included in the present invention. The preferred tracking system includes a slow tracking loop and a fast tracking loop, as discussed above. The tracking servo mirror 54 and the image comprise a part of both the fast tracking loop and the slow tracking loop. The slow tracking loop preferably includes the microprocessor control or CPU 110, sending signals to the tracking mirror 54, including the mirror drive, and is primarily limited in this embodiment of the invention by the maximum attainable video camera frame rate. The tracking mirror 54 controls the region of the target plane to be imaged as indicated. The image is fed to the fast tracking detector which is discussed above as the tracking camera 53a. This camera or detector sends information relating to position analysis to a dedicated logic analyzer or servo interface 54a capable of issuing command signals to the mirror 54 to adjust the mirror position to aim at the new position of the feature as determined by the processor 54a and the fast tracking detector or camera 53a. In accordance with the invention, this fast tracking preferably occurs at approximately 1 millisecond or faster response time, limited only by the response time of the mirror mount drives when loaded with the tracking mirror.

As shown in FIG. 5A, the microprocessor control or CPU 110 also sends signals to the tracking servo mirror and drive 54. This slow tracking loop includes the image, as shown in the drawing, and the profilometer camera 53b receiving the images. The profilometer camera 53b sends image information to the CPU 110, which is capable of finding a feature characteristically, if possible, whenever the fast tracking loop has lost the feature. The CPU 110 has the capability of searching for the feature in the entire field of view of the profilometer camera 53b and in generated cross-sectional topographic images, and issuing commands to the tracking servo mirror and drive 54 accordingly. The slow tracking loop further continuously tracks the depth as well as the position in the X-Y plane consistent with the three dimensional information derived from the profilometer camera 53b which constitutes the detector for the slow tracking loop. Hence, the slow tracking loop, in addition to acting as a backup mechanism for the fast tracking loop, also serves as the primary control system that adjusts the position, at the maximum video frame rate, of the front element of the final focusing lens 17.

As indicated in FIG. 5A, the dedicated microprocessor or other servo unit 54a issues an interrupt from the fast tracking loop to the CPU 110, when tracking of the feature is lost. Since both control signals (from the CPU 110 and from the dedicated microprocessor 54a) are always being fed to the tracking servo mirror and drive 54, the instructions from the CPU 110 take over when the fast tracking loop signal is interrupted. Normally, the unit 54 will operate on the fast tracking signal from the microprocessor 54a whenever that signal is being received, ignoring and overriding the other tracking signal from the CPU 110.

Tracking is considered to be effectively lost when a tracked feature of the image is not found from array signal frame to frame (or over a period of several frames) or if the feature progressively moves or drifts farther away from frame to frame. This latter event would signify that even though the feature is being tracked by the logic loop(s), instructions are not being properly carried out at the aiming mirrors. Examples of tracking loss not associated with the logic loop are failure of the signal to be effected by the servo drivers, required mirror motion exceeding the limiting displacement of the servo driven actuators, malfunction of the drivers or slides.

Figure 9:
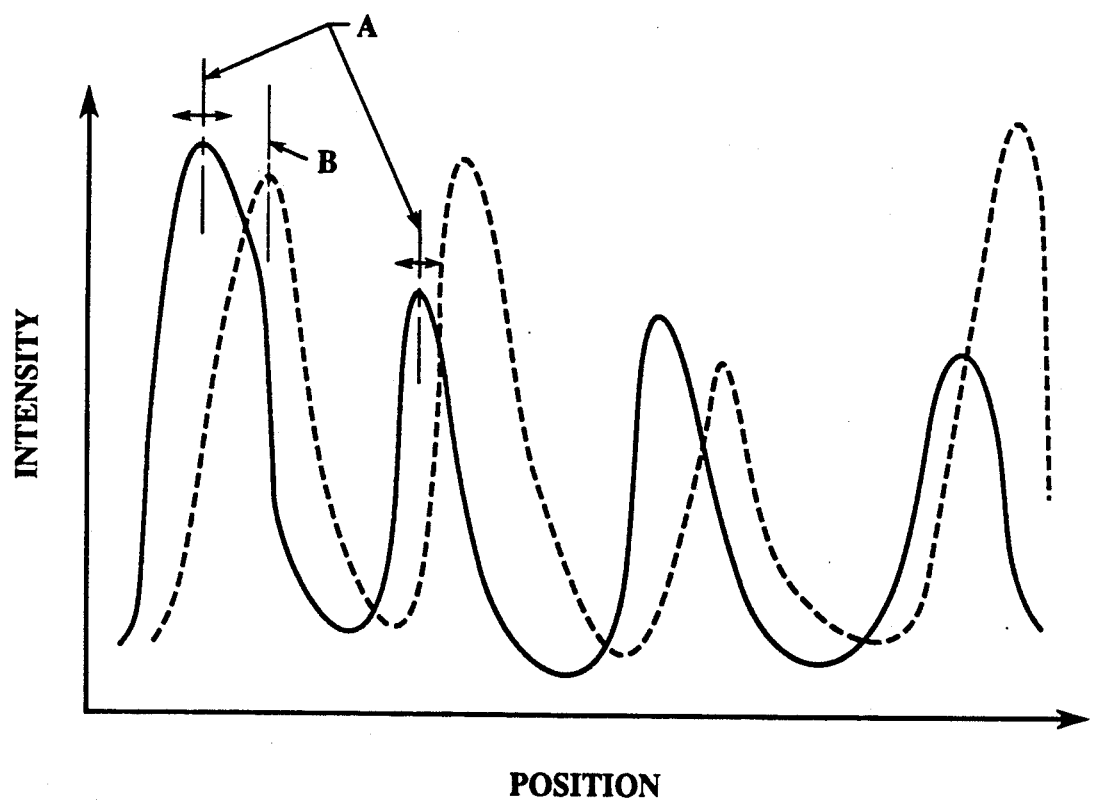
FIG. 9 is a graph plotting of light intensity versus position, relating to the imaging method shown in FIGS. 7 and 8.

FIG. 9 is an illustration of the manner in which the tracking system of the invention may function in one preferred embodiment. In this plotting of light intensity versus position, two curves appear corresponding to two different time scans indicating light intensity as detected by either one of the orthogonal linear scanning arrays of the fast tracking detectors. Curve A represents the light intensity pattern which might have been observed on a given small feature of the tissue, for example a feature on or in the eye, at an initial time A. Curve B represents a curve generally similar to curve A but shifted to the right. In one embodiment of the tracking system of the invention, the programming or fast tracking servo unit 54a recognizes that the pattern of curve A has shifted or at least has moved away from its initial position. The system then searches for a similar curve pattern, which because of orthogonal shifts usually will not be identical. If it finds scan function curve B is sufficiently similar to the previous scan function curve A that it must represent the same feature, then it issues an appropriate command to the tracking mirror via the dedicated servo processor to move to the new position. The new position is a correction input to the mirror via a correction signal based on the determined offset. Ordinarily the feature will not appear identical in the intensity curve such as shown in FIG. 9, because the feature will also have moved orthogonally with respect to the detector and will be seen by the camera from a slightly different viewpoint. However, the programming includes parameters enabling the system to recognize the shifted pattern as the feature, provided sufficient similarity exists within a selected range.

Figure 6:
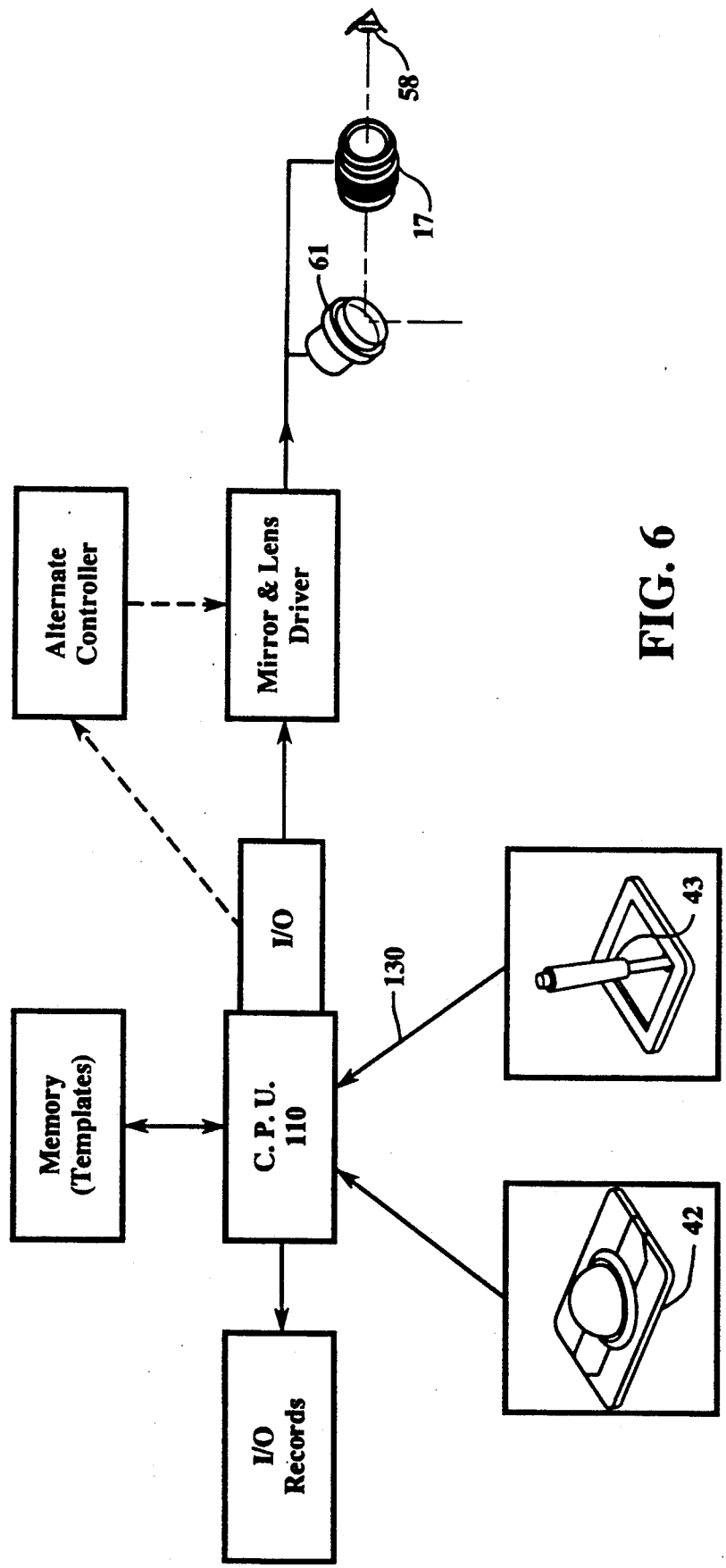
FIG. 6 is another block diagram indicating joystick and template information flow.

FIG. 6 is another functional block diagram, indicating joystick and template information. The joystick 43 is shown at the bottom of the figure. It sends signals along a line 130 to a central processing unit, which is the microprocessor 110. The CPU 110 is shown as connected to a number of other components. For example, it is shown as sending information to an I/O unit for record keeping. The transmissions may include, for example, patient history records to be printed or stored.

The ball mouse or Logimouse 42 is shown in FIG. 6, controlling templates, i.e. selecting pre-recorded templates or creating new ones for the surgery. In turn, the selected template information is put into the CPU.

The CPU 110 sends control signals to a dedicated I/O board 132 which is used for driving motors associated with the directional positioning mirror 61, as well as for driving Z-axis adjustments through the final focussing lens 17. The solid control line between the dedicated I/O board and the turning mirror 61 and final lens 17 indicates the use of the automated template procedure. On the other hand, as indicated in dashed lines, the surgery can be accomplished manually with the indicated optional manual override.

A commercially available dedicated I/O board 132 is capable of handling 16 analog channels and three digital channels in the currently described embodiment. It handles diagnostic information relating to laser status, position status, tracker mirror status, and other diagnostics which may be implemented as needed such as intraocular temperature, intraocular pressure readings, and surface wave propagation measurements to enable calculation of the Young's modulus and other elasticity constants in an effort to determine applicable constitutive relations. The sensors for these conditions of the eye are not shown in the drawings, but can be incorporated in the system of the invention.

Figure 6A:
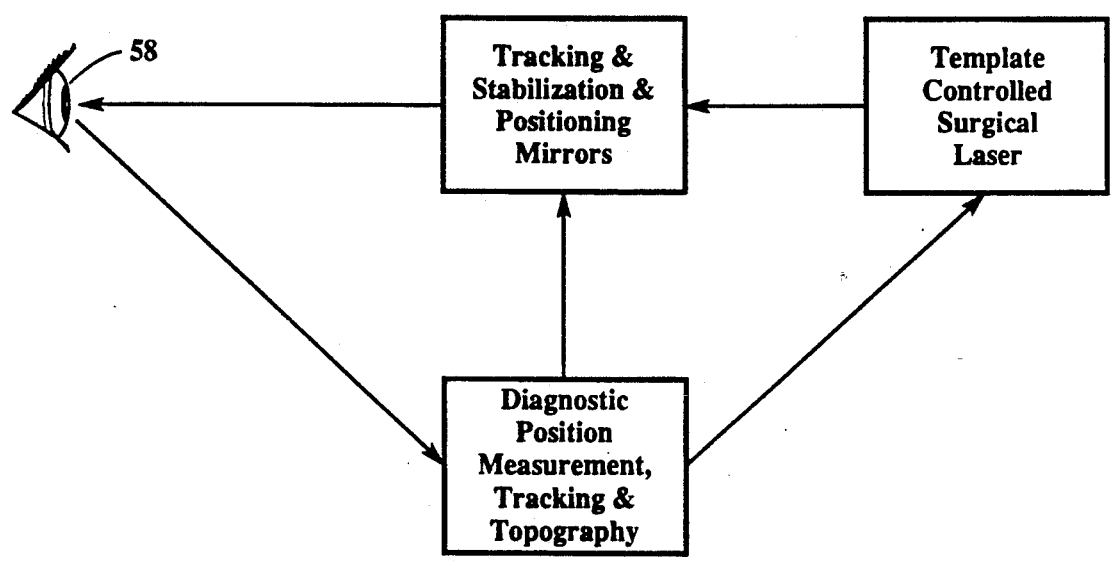
FIG. 6A is a further block diagram, illustrating the functional interdependence among certain subsystems of the invention.

FIG. 6A is another block diagram indicating operation of principal aspects of the system of the invention. FIG. 6A shows the looping of information and control signals in the system, particularly when a pre-programmed surgical template is used to control laser position and firing in the surgical procedure. In FIG. 6A the eye 58 is shown as sending information (via the tracking/profilometer camera 53, not shown) to a box labeled Diagnostic Position Measurement, Tracking and Topography. This indicates the derivation of such information from the eye via the camera and the microprocessor and programming 110 and 111 (FIG. 5). This block includes the sensors/cameras 53a and 53b and analysis loops, including the computer 110 and the dedicated microprocessor 54a. It includes tracking in the logic loop. The derived information relating to the topography of the eye tissues and the position of the camera on the eye is sent to the tracking and stabilization block which stabilizes the motions of the eye, relocating a feature after it has moved and repositioning the vision system to again be centered on the same feature. In FIG. 6A the Tracking and Stabilization block represents the tracking mirror 54 and the positioning mirror 61 (under template program control), as well as mirror drives for these mirrors.

FIG. 6A indicates the diagnostic position measurement and tracking block sending information to a block entitled template controlled surgical laser. This information comprises confirmation that the template is still positioned correctly, i.e. that the targeted feature of the eye has been tracked within a preselected time allotted, so that the images of the eye remain stabilized. If this confirmation is not sent (or a contrary signal could be sent to signal that tracking is lost), the template controlled laser firing is immediately interrupted, as discussed above.

The arrow from the template controlled laser toward the eye via the tracking servo mirror and positioning mirror merely indicates the conducting of the laser surgery on the eye via the two mirrors, and that the laser firing sequence is interrupted and discontinued in the event the tracking system loses stabilization of the image.

The arrow in FIG. 6A from the diagnostic position measurement block to the template controlled laser also indicates the feed of information, when called for by the surgeon, from the position measurement assembly to the template control system, to assist the surgeon in setting up a template as desired for the contemplated surgery. This information also assists the surgeon is positioning the template.

The Template Controlled Surgical Laser block in FIG. 6A should be considered as including the user interface, the computer and memory storage device relative to creating, modifying, storing, and executing surgical template programs.

FIG. 6A helps illustrate the interdependence of the three depicted subassemblies of the invention—the diagnostic position measurement and logic loop tracking, the tracking mirrors and the template controlled laser firing. FIG. 6A illustrates that all of these important components must operate in real time. None can operate with any significant delay, or the system would be rendered ineffective or unsafe. The diagnostic position measurement/tracking subsystem operates substantially instantaneously. The tracking system must recover the image position faster than the repetition rate of the laser. For many of the envisioned therapeutic uses of the present invention, it is preferable that the fast tracking system be capable of operating at or faster than 1 KHZ. Recovery of the image within a very short time period is necessary to enable the template-controlled surgery to proceed, since if any significant delay occurs, it would be unsafe to fire the laser—it could be fired at the wrong point.

The template controlled laser firing must also occur precisely in accordance with the preselected targeting sequence. It is the tracking system (including diagnostic, tracking and mirror movement) which is the critical link in this feedback loop shown in FIG. 6A. As noted above, if the tracking subsystem fails to move the servo controlled turning mirrors to maintain the target within acceptable error tolerances, then the template-controlled laser firing will be disabled until the images are again reacquired or until the surgeon re-initiates the program. Likewise, if an obstruction (such as a blinking eyelid for ophthalmic procedures or transient debris in cardiovascular procedures) were to interfere with the imaging/tracking light path (which also corresponds with the laser beam path), the template-controlled laser firing will be interrupted until the images again are acquired and the appropriate position in the template firing sequence is recovered.

FIGS. 7 and 8 indicate schematically one example of a three dimensional mapping system which may be used in conjunction with the vision system of the invention. In FIG. 3, 5 and 7 a Ronchi projector 21 is indicated, with a light source 126 shown projecting a light beam through a Ronchi ruling 127 as indicated. The Ronchi ruling may comprise a plurality of parallel equally spaced lines. The beam strikes the subject tissue, e.g. the eye 58, placing the ruling across several non-planar surfaces of the eye. The Ronchi projection beam is off-axis from the axis of the final focussing lens of the system, and FIG. 7 schematically indicates the tracking/profilometer camera 53 as being on-axis.

The profilometer camera 53b takes an image of the Ronchi projection from the non-planar surfaces of the eye, through a reference Ronchi grating schematically indicated at 128, and this image might appear, for example, as shown in FIG. 8. The so-called Moire fringes resulting from the interference (masking) between the projected and reference gratings or rulings appear as curved lines 129 as projected on the curved surfaces of the elements of the eye. In the preferred embodiment of the invention, an important feature is that the reference Ronchi grating or ruling resides in the computer memory and the interference (masking) occurs electronically on the detected image. The precise positioning of these curved lines can be analyzed to determine the precise shape and location of all elements illuminated by the Ronchi projection. Such analysis is well known to those skilled in the art and does not in itself form an important feature of the present invention, other than for the computer generated interference (masking) of the projected Ronchi grating or ruling with the computer generated reference grating or ruling.

As most surfaces in the eye are not only transparent but approximately spherical, a specular reflection from a fixed source can only reflect into an observing lens from a very small region of the surface. Thus, to see the entire surface simultaneously without filling the entire solid angle about the eye, it is preferred to detect the diffuse component of the reflection. Since the transparent surfaces of the eye have a very small diffuse component, an intensified camera is used to detect it without resorting to dangerous illumination levels (i.e. in the illuminator 51 shown in FIG. 3).

FIG. 7 further illustrates one preferred construction of the Ronchi projector. The light source 126 sends the beam through a UV and IR filter 132 and a condensing lens 133, as well as a polarizer 134. The filtered, polarized beam is then sent through the Ronchi ruling 127 and through a focussing lens 136 toward the eye 58 or other tissue to be operated upon. The light source 126 can comprise a diode laser or incandescent source.

The data generated from the projection of the Ronchi grating or ruling onto the target and back to the detectors (as illustrated in FIG. 7), when interfered electronically in the computer with the computer resident reference grating or ruling, yields interference (masking) fringes which are then analyzed by the microprocessor and programming to provide precise configurations along certain cross sectional lines, as desired.

In alternate embodiments of the invention, common or modified public domain specular techniques using distributed light sources may be used to generate certain mapping and profile data.

The system of the present invention is described without reference to details of construction, electronics and programming. These do not form specific parts, unless otherwise indicated, of the present invention and can be carried out by those skilled in the relevant arts.

The above described preferred embodiments are intended to illustrate the principles of the invention, but not to limit its scope. Other embodiments and variations to these preferred embodiments will be apparent to those skilled in the art, and may be made without departing from the scope of the invention as defined in the following claims.

We claim:

1. A system for use in ophthalmic diagnosis and analysis and for support of ophthalmic surgery, comprising, three dimensional mapping means for sensing locations, shapes and features on and in a patient's eye in three dimensions, and for generating data and signals representing such locations, shapes and features, display means receiving signals from the three dimensional mapping means, for presenting to a user images representative of said locations, shapes and features of the eye, at targeted locations including display control means for enabling a user to select the target location and to display a cross section of portions of the eye, position analysis means associated with and receiving signals from the three dimensional mapping means, for recognizing the occurrence of changes of position of features of the eye, target tracking means associated with the position analysis means, for searching for a feature of target tissue and finding said features new position after such a change of position, and for generating a signal indicative of the new position, and tracking positioning means for receiving said signal from the target tracking means and for executing a change in the aim of the three dimensional mapping means to the new position of said feature of the target tissue, to thereby follow the feature and stabilize the images on the display means.

2. The system of claim 1, wherein the display means is a video display, and further including surgical microscope means directed at the patient's eye, for taking video microscopic images of target areas of the ocular tissue and for feeding video image information to the video display means to cause such video microscopic images to be displayed, assisting the user in diagnosis and analysis.

3. The system of claim 1, further including display control means for enabling the user to cause to be displayed on the display means different cross sections of the patient's tissue, as selected by the user.

4. The system of claim 1, wherein the tracking positioning means includes a turning mirror under automatic control, and the system including an objective lens assembly associated with the mapping means and having a final focussing lens, with the turning mirror positioned within the objective lens assembly and movable with respect to the final focussing lens.

5. An instrument and system for high precision ophthalmic laser surgery at a surgical site, comprising, a laser pulsed source for producing a visible light laser beam having a power capable of effecting a desired type of surgery in an eye, laser firing control means for enabling a surgeon/user to control the aim, depth, and timing of the firing of the laser to effect the desired surgery, three dimensional mapping means directed at a patient's eye, for obtaining data representing the location and shapes of features on and inside the eye, microprocessor means for receiving data from the three dimensional mapping means and for converting the data to a format presentable on a screen and useful to the surgeon/user in precisely locating features of the eye and the aim and depth of the laser beam within those features, and display means for displaying microprocessor-generated images representing the topography of the eye and the aim and depth of the laser beam before the next pulse of the laser is fired to the surgeon/user in preparation for and during surgery, with display control means for enabling the surgeon/user to select areas of the eye for display, including images of cross sections of portions of the eye.

6. The instrument and system of claim 5, wherein the display means comprises a single video screen divided into multiple displays.

7. The instrument and system of claim 5, wherein the three dimensional mapping means, the microprocessor means, and the display means include means for presenting images to the surgeon/user indicating precise current location of laser aim and depth in computer generated views which comprise generally a plan view and selected cross sectional views of the eye representing features of the eye at different depths.

8. The instrument and system of claim 5, including an optical path with a focusing lens capable of controlling the focus of the laser beam on the eye tissue, and thus the depth at which the laser beam is effective, within about 5 microns, with depth control means for the surgeon to vary the focus of said lens to control the depth at which the laser beam is effective.

9. The instrument and system of claim 8, including system program means enabling the surgeon/user to pre-program a pattern of lesions in the ocular tissue along three axes in three dimensions and to activate the laser to follow the preselected pre-programmed path of surgery automatically.

10. The instrument and system of claim 5, further including tracking means for following movements of the eye during surgery and for following the movement of features at the surgical site of the eye with the three dimensional mapping means and with the laser, including means associated with the microprocessor for recognizing features at the surgical site after said features have moved and redirecting the three dimensional mapping system and the laser to the new location of said features.

11. The instrument and system of claim 10, wherein the display means includes a video monitor which has a frame rate and wherein the tracking means has the capability of following the features, identifying a new location of those features and re-presenting images of those features to the surgeon/user in a time period less than the frame rate of the video display means.

12. The instrument and system of claim 10, wherein the tracking means includes electromagnetically driven turning mirror means along an optical path of both the three dimensional mapping means and the laser beam, for shifting the aim of the three dimensional mapping means and a laser beam in response to the recognized to the recognized shift in position of the features of the eye.

13. The instrument and system of claim 10, wherein the display means comprises a video monitor which as a frame rate and the tracking means includes fast tracking means and backup slow tracking means with the backup slow tracking means including means for following the features at the surgical site, identifying a new location of said features and re-presenting images of said features to the surgeon/user in a time period at least as fast as the video frame rate, and the fast tracking means being capable of tracking movement of the tissue at much faster closed loop response times; and the backup slow tracking means having means for analyzing tissue position based on the three-dimensional topography of the tissue as determined, and for searching and finding, using the microprocessor means, a feature of the tissue when that feature is not found by the fast tracking means and for moving to the new position of the subject tissue feature and enabling the fast tracking means to recommence fast tracking.

14. The instrument and system of claim 5, wherein the display means comprises a video display monitor, and further including surgical microscope means on a common optical path with the laser beam, for obtaining a greatly enlarged image of a small region of the eye at which the laser beam is directed and for generating a video image of that small region for presentation on the display means.

15. The instrument and system of claim 14, wherein the surgical microscope means includes intensified video camera means for imaging at low light levels at high magnification while remaining within safe illumination levels for human clinical procedures.

16. The instrument and system of claim 14, wherein the display means comprises a video screen divided to show the image from the surgical microscope means as well as topography information obtained from the three dimensional mapping means and generated by said microprocessor means.

17. The instrument and system of claim 14, further including eye illumination means also along the common optical path with the laser beam, the surgical microscope and the three dimensional mapping means.

18. The instrument and system of claim 14, further including optical zooming mean associated with the surgical microscope means, for forming an image of adjustable magnification range of not less than tenfold increased magnification, of said small region of the eye with optical elements located a considerable and comfortable distance from the patient.

19. The instrument and system of claim 18, wherein the optical path includes a final focusing lens at the exterior of the instrument, with the final focusing lens positioned at least 100 mm from the patient's eye.

20. A system for facilitating precisely controlled surgery using a focused laser beam, comprising,
user interface means for presenting information to a surgeon/user and for enabling control of the surgical procedure by the surgeon/user, including video display means for presenting precise information to the surgeon/user relating to the location in a patient's tissue at which the system is targeted, and the three-dimensional topography and contours of features of the subject tissue and including means for displaying images of cross sections of portions of the patient's tissue, and including means in the control of the surgeon/user for scanning across the tissue to change the information on the video display means as desired by the surgeon/user and for enabling control of the firing of a surgical laser beam by the surgeon/user,
an imaging system connected to the video display means, including three-dimensional mapping means for generating, reading, and interpreting data to obtain information regarding the location in three dimensions of significant features of the tissue to be operated upon, and including microprocessor means for interpreting the data and presenting the data to the video display means in a format useful to the surgeon/user,
a short pulse visible light laser power source for generating a laser beam capable of effecting the desired laser surgery in the patient's tissue, including within transparent tissue of the patient,
optical path means for receiving the laser beam and redirecting the laser beam and focusing it as appropriate toward a desired target in the tissue to be operated upon,
surgical microscope means positioned to intercept and to be coaxial with the optical path means, for taking surgical microscopic images of said target along the optical path means and for feeding video image information to the video display means, and
tracking means in the optical path means and associated with the microprocessor means, for tracking movements of the subject tissue at which the system is targeted without damaging the subject tissue before the next pulse of the laser is fired and shifting the optical path means accordingly before the next pulse of the laser is fired, such that information and images generated by the three dimensional mapping mans and by the surgical microscope means, as well as the aiming and position of the laser beam, follow changes in position of the tissue.

21. The laser surgical system of claim 1, further including first control interlock means for preventing firing of the surgical laser beam except when the tracking means is properly tracking movements of the subject tissue at which the system is targeted, by preventing the laser from firing a next pulse of energy unless the tracking means has tracked the subject tissue.

22. The laser surgical system of claim 1, further including means for superimposing program templates over images created by the imaging system, for automatically effecting a pre-selected pattern of laser surgery.

23. The laser surgical system of claim 1, wherein the imaging system includes scattered light detection means for detecting scattered light from the features of the tissue, with means for filtering out substantially all specularly-reflected light for the scattered light detection means.

24. The laser surgical system of claim 1, wherein the surgical microscope means includes an intensified video camera means for imaging at low light levels at high magnification while remaining within safe illumination levels for human clinical procedures.

25. The laser surgical system of claim 1, wherein the optical path means includes a final focussing lens with means for focussing the laser beam, the three dimensional mapping means and the surgical microscope means an appreciable and comfortable distance from the final focussing lens with respect to the patient, a distance of not less than about 50 mm.

26. The laser surgical system of claim 25, including an objective lens assembly of which the final focussing lens comprises a front element, and wherein the tracking means includes a turning mirror under automatic control of the microprocessor means, with the turning mirror positioned within the objective lens assembly and movable with respect to the final focussing lens.

27. The laser surgery system of claim 1, including tracking and profilometer camera means associated with the three dimensional mapping means and with the tracking means, also intercepting and directed along said optical path means and having an angle of view, for obtaining data from the patient's tissue along said optical path means and for sending data to the microprocessor means of the imaging system, for generation of topographical information to the presented on the video display means.

28. The laser surgery system of claim 27, wherein the tracking means includes a electromagnetically driven turning mirror which affects the angle of view of the tracking and profilometer camera means and also the aim of the surgical microscope means and the laser beam, the electromagnetically driven mirror being under the control of signals generated by the microprocessor means of the imaging system to follow recognized features of the patient's tissues after movement of that tissue.

29. The laser surgery of claim 1, wherein the tracking means includes fast tracking means for tracking movements of the tissue at tracking closed loop response times of one millisecond or less.

30. The laser surgery system of claim 29, wherein the tracking means further includes backup slow tracking means for analyzing tissue position based on the three-dimensional topography of the tissue as determined, and for searching and finding, using the microprocessor means, a feature of the tissue when that feature is not found by the fast tracking means within a predetermined time and for shifting the optical path means to reposition the optical path means on the tissue feature.

31. The laser surgery system of claim 30, wherein the backup slow tracking means includes a video camera having a frame rate, and wherein the slow tracking means operates at tracking closed loop response times equal to the video camera frame rate.

32. A system for use in ophthalmic laser surgery, comprising,
  a laser source for producing a pulsed visible light laser beam having a power capable of effecting a desired type of surgery at targeted tissue at a selected surgical site in the ocular tissues,
  optical path means for delivering the laser beam, including beam directing means for controlling aim and depth of focus of the laser beam,
  three dimensional mapping means for sensing locations, shapes and features on and in a patient's eye in three dimensions, and for generating data and signals representing such locations, shapes and features,
  display means receiving signals from the three dimensional mapping means, for presenting to a surgeon user images representative of said locations, shapes and features of the eye including at depths in the eye selectable by the surgeon,
  position analysis means associated with and receiving signals from the three dimensional mapping means, for recognizing the occurrence of changes of position of features of targeted tissue of the eye,
  target tracking means associated with the position analysis means, for searching for a feature of targeted tissue and finding the feature's new position after such a change of position, and for generating a signal indicative of the new position of the targeted feature tissue, and
  tracking positioning means for receiving said signal from the target tracking mean and for executing a change in the aim of the three dimensional mapping means to the new position of a targeted tissue feature to thereby follow the feature and stabilize the images on the display means, and for simultaneously and accordingly adjusting the aim of the laser beam to be directed at a new position of the targeted feature.

33. The system of claim 32, further including pre-programmed surgery execution means for automatically controlling timing of laser firing in conjunction with automatically controlling the beam directing means as to laser aim and depth of focal point in accordance with a preselected surgical path in three dimensions, to fully automatically execute a selected surgical procedure on the eye, and including tracking feedback means associated with the target tracking means and the surgery execution means, for sending signals to the pre-programmed surgery execution means to confirm that a feature's new position has been found, and to discontinue laser firing if such a confirming signal is not received by the surgery execution means within a preselected period of time.

34. The system of claim 32, wherein the display means is a video display monitor, and further including surgical microscope means positioned to intercept and to be coaxial with the optical path means, for taking video microscopic images of target areas of the ocular tissue and for feeding video image information to the video display monitor to cause such video microscopic images to be displayed, assisting the surgeon in the laser surgery.

35. The system of claim 32, further including surgeon control means connected to the beam directing means for enabling a surgeon user to control the aim and depth of focus of the laser beam.

36. A method for conducting laser surgery, comprising,
  providing a system for imaging a patient's tissue in three dimensions, displaying images is selected formats on a display screen in front of a surgeon, delivering a visible light laser beam at the patient's tissue and firing the laser in accordance with a surgical path in three dimensions as selected by the surgeon directing the laser and for tracking the patient's tissue so as to stabilize images presented on the display screen and to essentially immobilize the subject target tissue on the display screen in spite of actual movements of the tissue,
  placing a patient adjacent to the system,
  under control of the surgeon, reviewing the patient's tissue at different locations and along different cross-sections by selection of desired images on the display screen,
  under control of the surgeon, selecting a surgical path in three dimensions for surgery on the subject tissue and comprising a series of locations for targeting the focal point of and firing the laser beam to effect the surgery, and entering the precise surgical path as selected by the surgeon into a computer and memory of the system,
  under control of the surgeon, initiating the firing of the laser along the programmed surgical path selected by the surgeon, and
  automatically interrupting the surgery along the programmed surgical path whenever the tracking device of the system has failed to relocate a moved tissue feature within a pre-selected period of time.

37. The method of claim 36, further including the surgeon's surveying video microscopic images of the subject ocular tissue along with the other images displayed on the screen, as a guide to the surgeon in controlling the laser surgery, using a surgical microscope which views the patient's eye tissue at substantially the same region viewed by the three dimensional imaging system, with the system having means for presenting a video microscopic image of the subject targeted tissue on the display screen.

38. A method for conducting ophthalmic laser surgery using an imaging system which displays for the surgeon precise information as the location and configuration of features of the patient's eye and as to the aim and depth of focal point of a surgical laser beam, comprising, generating with a laser source a visible light laser beam having a power capable of effecting a desired type of surgery in the eye, delivering the laser beam along an optical path, controlling aim and depth of focus of the laser beam with a beam directing means associated with the laser optical path, sensing locations, shapes and features on and in a patient's eye in three dimensions with a three dimensional mapping means, and generating data and signals representing such locations, shapes and features, presenting to a surgeon user images representative of said locations, shapes and features of the eye at the target site, on a display mans which receives signals from the three dimensional mapping means including images of cross sections of portions of the eye, recognizing the occurrence of changes of position of features of the at the targeted site, with a position analysis means associated with and receiving signals from the three dimensional mapping means, searching for a target site feature and finding the target site feature's new position after such a change of position ,and generating a signal indicative of the new position, with a target tracking means associated with the position analysis means, and automatically executing a change in the aim of the three dimensional mapping means to the new position of the feature with a tracking positioning means receiving said signal from the target tracking means, to thereby follow the target site feature and stabilize the images on the display means, and simultaneously and accordingly adjusting automatically the aim and depth of the focus of the laser beam to be directed at the new position of a feature targeted.

39. The method of claim 38, further including the step of reviewing by the surgeon different cross-sections of the ocular tissues by manually selecting different formats to be presented on the display means.

40. The method of claim 38, further including monitoring the patient's tissue with a surgical microscope, and sending signals from the surgical microscope to the display means to present video display of greatly magnified images of the eye tissue, with the surgical microscope sharing a common optical path with the laser beam, including a final focussing lens, such that the video microscopic images displayed comprise a microscopic region at the same location and focal depth that the laser beam is directed.

41. The method of claim 40, including illuminating the patient's eye tissue at a low light level within a safe illumination level for human clinical procedures for said monitoring of the patient's tissue on the video display, the surgical microscope including an intensified video camera for imaging at low light levels at high magnification.

42. The method of claim 38, further including performing laser ophthalmic surgery automatically, in accordance with pre-programmed surgical paths in three dimensions, by selecting a software-based surgical path and initiating the program to automatically aim, focus and fire the laser sequentially at the preselected points establishing the surgical path.

43. The method of claim 42, further including automatically interrupting the aiming and firing of the laser along the pre-programmed path whenever the target tracking means fails to relocate a moved feature within a preselected period of time, thereby interrupting the execution of the pre-programmed surgery immediately when the ocular features subjected to the surgery become transposed an unsafe distance from the intended focal point of the laser beam.

44. The method of claim 42, wherein the system includes surgeon-controlled means for writing and editing pre-programmed surgical path templates, and the method including the surgeon's writing a pre-programmed surgical template before initiating the automatic execution of the surgery along the pre-programmed path.

* * * * *

UNITED STATES PATENT AND TRADEMARK OFFICE
CERTIFICATE OF CORRECTION

PATENT NO. : 5,098,426
DATED : March 24, 1992
INVENTOR(S) : Sklar et al.

It is certified that error appears in the above—identified patent and that said Letters Patent is hereby corrected as shown below:

Column 29, line 26:

Correct "features" to read --feature's--

Column 30, line 58:

Correct "a laser beam" to read --the laser beam--

Column 30, lines 58 - 59:

correct "the recognized to the" to read --a--

Column 30, line 62:

Correct "as" to read --has--

Column 31, lines 10 - 11:

Correct " torecommence" to read --to recommence--

Column 31, line 28:

Correct "topography" to read --topographical--

Column 31, line 36:

Correct "mean" to read --means--

Column 32, line 25:

Correct "mans" to read --means--

UNITED STATES PATENT AND TRADEMARK OFFICE
CERTIFICATE OF CORRECTION

PATENT NO. : 5,098,426
DATED : March 24, 1992
INVENTOR(S) : Sklar et al.

Page 2 of 3

It is certified that error appears in the above—identified patent and that said Letters Patent is hereby corrected as shown below:

Column 32, line 28:

Correct "claim 1" to read --claim 20--

Column 32, line 29:

Correct "first" to read --fire--

Column 32, lines 35, 40, 46, 51, and 65

Correct "claim 1" to read --claim 20

Column 33, line 17:

Correct "claim 1" to read --claim 20--

Column 33, line 65:

Correct "mean" to read --means--

Column 34, line 36:

Correct "is" to read --in--

Column 35, line 27:

Correct "mans" to read --means--

Column 35, line 31:

Correct "of the at" to read --of the eye at--

UNITED STATES PATENT AND TRADEMARK OFFICE
CERTIFICATE OF CORRECTION

PATENT NO. : 5,098,426

DATED : March 24, 1992

INVENTOR(S) : Sklar et al.

It is certified that error appears in the above—identified patent and that said Letters Patent is hereby corrected as shown below:

Column 35, line 42:

Correct "the feature" to read --the target site feature-- column 36, line 10:

Correct "present video" to read --present a video--

Signed and Sealed this

Third Day of August, 1993

Attest:

MICHAEL K. KIRK

Attesting Officer     Acting Commissioner of Patents and Trademarks